(12) United States Patent
Kim et al.

(10) Patent No.: US 12,037,589 B2
(45) Date of Patent: Jul. 16, 2024

(54) AMPHIREGULIN GENE-SPECIFIC DOUBLE-STRANDED OLIGONUCLEOTIDE AND COMPOSITION FOR PREVENTING AND TREATING FIBROSIS-RELATED DISEASES AND RESPIRATORY DISEASES, COMPRISING SAME

(71) Applicant: Bioneer Corporation, Daejeon (KR)

(72) Inventors: Tae-Rim Kim, Daejeon (KR); Pyoung Oh Yoon, Daejeon (KR); Youngho Ko, Seoul (KR); Seon Joo Bae, Chungcheongnam-do (KR); Han-Oh Park, Sejong-si (KR); Seung Seob Son, Chungcheongnam-do (KR); Jun-Hong Park, Daejeon (KR); Sung-Il Yun, Daejeon (KR)

(73) Assignee: Bioneer Corporation, Daejeon (KR)

( * ) Notice: Subject to any disclaimer, the term of this patent is extended or adjusted under 35 U.S.C. 154(b) by 0 days.

(21) Appl. No.: 18/330,853

(22) Filed: Jun. 7, 2023

(65) Prior Publication Data

US 2023/0332154 A1 Oct. 19, 2023

Related U.S. Application Data

(63) Continuation of application No. 18/067,363, filed on Dec. 16, 2022, now abandoned, which is a continuation of application No. 17/057,852, filed as application No. PCT/KR2019/006144 on May 22, 2019, now abandoned.

(30) Foreign Application Priority Data

May 25, 2018 (KR) .......................... 10-2018-0059783

(51) Int. Cl.
| | |
|---|---|
| *C12N 15/11* | (2006.01) |
| *A61K 9/19* | (2006.01) |
| *A61K 31/713* | (2006.01) |
| *A61P 11/00* | (2006.01) |
| *C12N 15/113* | (2010.01) |

(52) U.S. Cl.
CPC ............ *C12N 15/1136* (2013.01); *A61K 9/19* (2013.01); *A61K 31/713* (2013.01); *A61P 11/00* (2018.01); *C12N 2310/14* (2013.01); *C12N 2310/314* (2013.01); *C12N 2310/322* (2013.01); *C12N 2310/351* (2013.01); *C12N 2310/3515* (2013.01)

(58) Field of Classification Search
CPC .............. A61K 31/713; C12N 2310/14; C12N 2310/351
See application file for complete search history.

(56) References Cited

U.S. PATENT DOCUMENTS

| | | | |
|---|---|---|---|
| 5,660,985 | A | 8/1997 | Pieken et al. |
| 5,808,023 | A | 9/1998 | Sanghvi et al. |
| 5,958,691 | A | 9/1999 | Pieken et al. |
| 6,175,001 | B1 | 1/2001 | Barbas et al. |
| 6,326,358 | B1 | 12/2001 | Manoharan |
| 6,531,584 | B1 | 3/2003 | Cook et al. |
| 2006/0246448 | A1 | 11/2006 | Ullrich et al. |
| 2007/0037228 | A1 | 2/2007 | Moecks et al. |
| 2010/0112603 | A1 | 5/2010 | Moecks et al. |
| 2013/0034565 | A1 | 2/2013 | Lindzen et al. |
| 2017/0130231 | A1 | 5/2017 | Chae et al. |
| 2018/0148727 | A1 | 5/2018 | Grund et al. |
| 2019/0345504 | A1 | 11/2019 | Grund et al. |

FOREIGN PATENT DOCUMENTS

| | | | |
|---|---|---|---|
| CN | 101705287 | A | 5/2010 |
| CN | 106459974 | A | 2/2017 |
| CN | 107124889 | A | 9/2017 |
| EA | 020335 | B1 | 10/2014 |
| EP | 2905337 | A1 | 8/2015 |
| EP | 3128008 | A2 | 2/2017 |
| JP | 2010-505934 | A | 2/2010 |
| JP | 2017-512502 | A | 5/2017 |
| JP | 2021-525103 | A | 9/2021 |
| KR | 10-0883471 | B1 | 2/2009 |
| KR | 10-2012-0080562 | A | 7/2012 |
| KR | 10-1224828 | B1 | 1/2013 |
| KR | 10-2015-0064065 | A | 6/2015 |
| KR | 10-2015-0115687 | A | 10/2015 |
| WO | WO 2014/054927 | A1 | 4/2014 |
| WO | WO-2016204515 | A1 * | 12/2016 ............. A61K 48/00 |

OTHER PUBLICATIONS

WO 2016/204515 machine translation, pp. 1-38 (Year: 2016).*
Akhtar, S., et al.., "Nonviral delivery of synthetic siRNAs in vivo", "The Journal of Clinical Investigation", Dec. 2007, pp. 3623-3632, vol. 117, No. 12, Publisher: http//www.jci.org.
Amarzguioui, M., et al.., "Tolerance for mutations and chemical modifications in a siRNA", "Nucleic Acid Research", 2003, pp. 589-595, vol. 31, No. 2, Publisher: Oxford University Press.
Aw, M.S., et al., "Polymeric Micelles for Multidrug Delivery and Combination Therapy", Chemistry European Journal, 2013, pp. DOI: 10, 1002/chem.201302097, vol. 00, No. 0-0, Publisher: Wiley-VCH Verlag Gmbh & Co. KGaA, Weinheim.

(Continued)

*Primary Examiner* — Ekaterina Poliakova-Georgantas
(74) *Attorney, Agent, or Firm* — Fenwick & West LLP

(57) ABSTRACT

The present invention relates to a double-stranded oligonucleotide which can highly specifically and efficiently inhibit an amphiregulin expression and, preferably, a double-stranded oligonucleotide comprising a sequence in the form of RNA/RNA, DNA/DNA or DNA/RNA hybrid, a double-stranded oligonucleotide structure comprising the double-stranded oligonucleotide, nanoparticles comprising the double-stranded oligonucleotide structure, and a fibrosis or respiratory disease preventive or therapeutic use thereof.

17 Claims, 14 Drawing Sheets
(12 of 14 Drawing Sheet(s) Filed in Color)
Specification includes a Sequence Listing.

(56) References Cited

OTHER PUBLICATIONS

Baillo, A., et al.., "Knock-Down of Amphiregulin inhibits Cellular Invasion in inflammatory Breast Cancer", "Journal of Cellular Physiology", 2011, pp. 2691-2701, vol. 226, No. 10, Publisher: Wiley-Liss, Inc.

Barik, S., "Silence of the transcripts: RNA interference in medicine", "J Mol Med", 2005, pp. 764-773, vol. 83, Publisher: Springer-Verlag 2005.

Bates, D.V., "Respiratory Disease: Definition, Causes & Types", Britannica, Jul. 27, 2017, https://www.britannica.com/science/respiratory-disease.

Behlke, M., "Progress Towards in Vivo Use of siRNAs", "Molecular Therapy", Apr. 2006, pp. 644-670, vol. 13, No. 4, Publisher: The American Society of Gene Therapy.

Braasch, D.A., et al.., "Biodistribution of phosphodiester and phosphorothioate siRNA", "Bioorganic & Medicinal Chemistry Letters," 2004, pp. 1139-1143, vol. 14, Publisher: Elsevier.

Bramsen, J.B., et al., "A screen of chemical modifications identifies position-specific modification by UNA to most potential reduce siRNA off-target effects", "Nucleic Acids Research", 2010, pp. 5761-5773, vol. 38, No. 17, Publisher: Oxford University Press.

Chery, J., "RNA therapeutics: RNAi and antisense mechanisms and clinical applications", "Journal of Postdoctoral Research", Jul. 2016, pp. 35-50, vol. 4, No. 7, Publisher: www.PostdocJournal.com.

Chiu, Y-L, et al, "siRNA function in RNAi: A chemical modification analysis", "RNA", 2003, pp. 1034-1048, vol. 9, Publisher: Cold Spring Harbor Laboratory Press.

Crooke, S., "Progress in Antisense Technology", "Annu. Rev. Med.", 2004, pp. 61-95, vol. 55, Publisher: Annual Reviews.

Deacon, K., et al., "Human airway smooth muscle cells secrete amphiregulin via bradykinin/COX-2/PGE2, inducing COX-2, CXCL8, and VEGF expression in airway epithelial cells", Am J Physiol Lung Cell Mol Physiol, 2015, Page(s) doi: 10.1152/ajplung.00390.2014, vol. 309.

Ding, L., et al., "Bone Marrow CD11 c+ Cell-Derived Amphiregulin Promotes Pulmonary Fibrosis", The Journal of Immunology, 2016, pp. 303-312, vol. 197, Publisher: American Association of Immunologists.

Duffield, J., "Cellular and molecular mechanisms in kidney fibrosis", The Journal of Clinical Investigation, pp. 2299-2306, vol. 124, No. 6, Publisher: http://www.jci.org 2014.

Eckstein, N., et al., "Epidermal Growth Factor Receptor Pathway Analysis Identifies Amphiregulin as a Key Factor for Cisplatin Resistance of Human Breast Cancer Cells", Journal of Biological Chemistry, 2008, pp. 739-750, vol. 283, No. 2, Publisher: The American Society for Biochemistry and Molecular Biology.

Hohjoh, H., "RNA interference (RNAi) induction with various types of synthetic oligonucleotide duplexes in cultured human cells," FEBS Letters, 2002, vol. 521, pp. 195-199, Publisher: Elsevier Science B.V.

Kim, H., et al., "Polymer-Based Hybrid Materials for Gene Delivery and Silencing", "Polymer Science and Technology", 2011, pp. 259-259, vol. 23, No. 3, Publisher: Department of Chemistry, Postech.

Kim, S., et al., "Local and systemic: delivery of VEGF siRNA using polyelectrolyte complex micelles for effective treatment of cancer", "Journal of Controlled Release", 2008, pp. 107-116, vol. 129, Publisher: Elsevier.

Kim, S., et al., "Overcoming the barriers in micellar drug delivery: loading efficiency, in vivo stability, and micelle-cell interaction", Expert Opinion Drug Delivery, 2010, pp. 49-62, vol. 7, No. 1, Publisher: Informa UK Ltd.

Livak, K.J., et al, "Analysis of Relative Gene Expression Data Using Real-Time Quantitative PCR and the 2-CT Method", "Methods", 2001, pp. 402-408, vol. 25, Publisher: Elsevier Science.

Lombardo, D., et al., "Amphiphiles Self-Assembly: Basic Concepts and Future Perspectives of Supramolecular Approaches", Advances in Condensed Matter Physics, 2015, Page(s) doi.org/10.1155/2015/151683, vol. 2015, No. ID 151683, Publisher: Hindawi Publishing Corporation.

Mantero, M., et al., "Antibiotic therapy, supportive treatment and management of immunomodulation-inflammation response in community acquired pneumonia: review of recommendations", Multidisciplinary Respiratory Medicine, 2017, Page(s) DOI 10.1186/s40248-017-0106-3, vol. 12, No. 26, Publisher: CrossMark.

Mattila, J., et al., "Pneumonia Treatment and Diagnosis", Ann Am Thorac Soc, 2014, pp. S189-S192, vol. 11, No. 4, Publisher: American Thoracic Society.

Schmucker, H., et al., "Amphiregulin regulates proliferation and migration of HER2-positive breast cancer cells", Cellular Oncology, 2018, pp. 159-168, vol. 41, Publisher: Springer.

Shigeta, K., et al., "Novel histidine-conjugated galactosylated cationic liposomes for efficient hepatocyte-selective gene transfer in human hepatoma HepG2 cells", "Journal of Controlled Release", 2007, pp. 262-270, vol. 118, Publisher: Elsevier.

Soutschek, J., et al., "Therapeutic silencing of an endogenous gene by systemic administration of modified siRNAs", "Nature", Nov. 2004, pp. 173-178, vol. 432, Publisher Nature Publishing Group.

Taniguchi, H., et al., "Amphiregulin triggered epidermal growth factor receptor activation confers in vivo crizotinib-resistance of EML4-ALK lung cancer and circumvention by epidermal growth factor receptor inhibitors", Cancer Science, 2017, pp. 53-60, vol. 108, Publisher: Japanese Cancer Association.

Vaish, N., et al, "Improved specificity of gene silencing by siRNAs containing unlocked nucleobase analogs", "Nucleic Acids Research", 2011, pp. 1823-1832, vol. 39, No. 5, Publisher: Oxford University Press.

Veronese, F.M., et al., "PEGylation, successful aproact1 to drug delivery", "Drug Discovery Today", Dec. 2005, pp. 1451-1458, vol. 10, No. 21, Publisher: Elsevier.

Wynn, T., et al., "Mechanisms offibrosis: therapeutic translation for fibrotic disease", Nature Medicine, 2012, pp. 1028-1040, vol. 18, No. 7, Publisher: NPG.

Xie, F., et al., "Harnessing in vivo siRNA delivery for drug discovery and therapeutic development", "Drug Discovery Today", 2006, pp. 67-73, vol. 11, No. 1/ 2, Publisher: Elsevier.

Yoon, O.P., et al., "Self-assembled Michelle Interfering RNA for Effective and Safe Targeting of Dysregulated Genes in Pulmonary Fibrosis", JBC Papers in Press, 2016, Page(s) doi/10.1074/jbc.M115.693671, vol. M115.693671, Publisher: The American Society for Biochemistry and Molecular Biology, Inc.

Son, B. et al., "SAMiRNA Targeting Amphiregulin Alleviate Total-Body-Irradiation-Induced Renal Fibrosis," Radiation Research 197(5), May 2022, pp. 471-479.

* cited by examiner

DNA/RNA Hybrid SAMiRNA

RNA/RNA Hybrid SAMiRNA

SEQUENCE LISTING

```
Sequence total quantity: 48
SEQ ID NO: 1            moltype = DNA  length = 19
FEATURE                 Location/Qualifiers
source                  1..19
                        mol_type = other DNA
                        organism = synthetic construct
SEQUENCE: 1
cctataaagc ggcaggtgc                                                   19

SEQ ID NO: 2            moltype = DNA  length = 19
FEATURE                 Location/Qualifiers
source                  1..19
                        mol_type = other DNA
                        organism = synthetic construct
SEQUENCE: 2
gagcggcgca cactcccgg                                                   19

SEQ ID NO: 3            moltype = DNA  length = 19
FEATURE                 Location/Qualifiers
source                  1..19
                        mol_type = other DNA
                        organism = synthetic construct
SEQUENCE: 3
```

```
gtcccagaga ccgagttgc                                                      19

SEQ ID NO: 4            moltype = DNA   length = 19
FEATURE                 Location/Qualifiers
source                  1..19
                        mol_type = other DNA
                        organism = synthetic construct SEQUENCE: 4
gagacgccgc cgctgcgaa                                                      19

SEQ ID NO: 5            moltype = DNA   length = 19
FEATURE                 Location/Qualifiers
source                  1..19
                        mol_type = other DNA
                        organism = synthetic construct SEQUENCE: 5
ccggcgccgg tggtgctgt                                                      19

SEQ ID NO: 6            moltype = DNA   length = 19
FEATURE                 Location/Qualifiers
source                  1..19
                        mol_type = other DNA
                        organism = synthetic construct SEQUENCE: 6
ggtggtgctg tcgctcttg                                                      19

SEQ ID NO: 7            moltype = DNA   length = 19
FEATURE                 Location/Qualifiers
source                  1..19
                        mol_type = other DNA
                        organism = synthetic construct SEQUENCE: 7
cgctcttgat actcggctc                                                      19

SEQ ID NO: 8            moltype = DNA   length = 19
FEATURE                 Location/Qualifiers
source                  1..19
                        mol_type = other DNA
                        organism = synthetic construct SEQUENCE: 8
tcttgatact cggctcagg                                                      19

SEQ ID NO: 9            moltype = DNA   length = 19
FEATURE                 Location/Qualifiers
source                  1..19
                        mol_type = other DNA
                        organism = synthetic construct SEQUENCE: 9
ggacctcaat gacacctac                                                      19

SEQ ID NO: 10           moltype = DNA   length = 19
FEATURE                 Location/Qualifiers
source                  1..19
                        mol_type = other DNA
                        organism = synthetic construct SEQUENCE: 10
cacctactct gggaagcgt                                                      19

SEQ ID NO: 11           moltype = DNA   length = 19
FEATURE                 Location/Qualifiers
source                  1..19
                        mol_type = other DNA
                        organism = synthetic construct SEQUENCE: 11
acctactctg ggaagcgtg                                                      19

SEQ ID NO: 12           moltype = DNA   length = 19
FEATURE                 Location/Qualifiers
source                  1..19
                        mol_type = other DNA
                        organism = synthetic construct SEQUENCE: 12
ctgggaagcg tgaaccatt                                                      19

SEQ ID NO: 13           moltype = DNA   length = 19
FEATURE                 Location/Qualifiers
source                  1..19
                        mol_type = other DNA
                        organism = synthetic construct
```

```
SEQUENCE: 13
gaagcgtgaa ccatttct                                                    19

SEQ ID NO: 14         moltype = DNA   length = 19
FEATURE               Location/Qualifiers
source                1..19
                      mol_type = other DNA
                      organism = synthetic construct
SEQUENCE: 14
ttctggggac cacagtgct                                                   19

SEQ ID NO: 15         moltype = DNA   length = 20
FEATURE               Location/Qualifiers
source                1..20
                      mol_type = other DNA
                      organism = synthetic construct
SEQUENCE: 15
ggtgaaggtc ggagtcaacg                                                  20

SEQ ID NO: 16         moltype = DNA   length = 25
FEATURE               Location/Qualifiers
source                1..25
                      mol_type = other DNA
                      organism = synthetic construct
SEQUENCE: 16
accatgtagt tgaggtcaat gaagg                                            25

SEQ ID NO: 17         moltype = DNA   length = 20
FEATURE               Location/Qualifiers
source                1..20
                      mol_type = other DNA
                      organism = synthetic construct
SEQUENCE: 17
acacctactc tgggaagcgt                                                  20

SEQ ID NO: 18         moltype = DNA   length = 20
FEATURE               Location/Qualifiers
source                1..20
                      mol_type = other DNA
                      organism = synthetic construct
SEQUENCE: 18
gccaggtatt tgtggttcgt                                                  20

SEQ ID NO: 19         moltype = DNA   length = 19
FEATURE               Location/Qualifiers
source                1..19
                      mol_type = other DNA
                      organism = synthetic construct
SEQUENCE: 19
aacgggactg tgcatgcca                                                   19

SEQ ID NO: 20         moltype = DNA   length = 19
FEATURE               Location/Qualifiers
source                1..19
                      mol_type = other DNA
                      organism = synthetic construct
SEQUENCE: 20
acgggactgt gcatgccat                                                   19

SEQ ID NO: 21         moltype = DNA   length = 19
FEATURE               Location/Qualifiers
source                1..19
                      mol_type = other DNA
                      organism = synthetic construct
SEQUENCE: 21
cagttgtcac ttttatga                                                    19

SEQ ID NO: 22         moltype = DNA   length = 21
FEATURE               Location/Qualifiers
source                1..21
                      mol_type = other DNA
                      organism = synthetic construct
SEQUENCE: 22
aggtcggtgt gaacggattt g                                                21

SEQ ID NO: 23         moltype = DNA   length = 23
FEATURE               Location/Qualifiers
source                1..23
                      mol_type = other DNA
```

-continued

```
                         organism = synthetic construct
SEQUENCE: 23
tgtagaccat gtagttgagg tca                                              23

SEQ ID NO: 24            moltype = DNA   length = 20
FEATURE                  Location/Qualifiers
source                   1..20
                         mol_type = other DNA
                         organism = synthetic construct
SEQUENCE: 24
gaggcttcga caagaaaacg                                                  20

SEQ ID NO: 25            moltype = DNA   length = 20
FEATURE                  Location/Qualifiers
source                   1..20
                         mol_type = other DNA
                         organism = synthetic construct
SEQUENCE: 25
accaatgtca tttccggtgt                                                  20

SEQ ID NO: 26            moltype = DNA   length = 21
FEATURE                  Location/Qualifiers
source                   1..21
                         mol_type = other DNA
                         organism = synthetic construct
SEQUENCE: 26
cagtgctgat ggatttgagg t                                                21

SEQ ID NO: 27            moltype = DNA   length = 22
FEATURE                  Location/Qualifiers
source                   1..22
                         mol_type = other DNA
                         organism = synthetic construct
SEQUENCE: 27
atagccaggt atttgtggtt cg                                               22

SEQ ID NO: 28            moltype = DNA   length = 23
FEATURE                  Location/Qualifiers
source                   1..23
                         mol_type = other DNA
                         organism = synthetic construct
SEQUENCE: 28
tgaaccgtcc tcgggagccg act                                              23

SEQ ID NO: 29            moltype = DNA   length = 20
FEATURE                  Location/Qualifiers
source                   1..20
                         mol_type = other DNA
                         organism = synthetic construct
SEQUENCE: 29
gtgtttgacg gcatcccacc                                                  20

SEQ ID NO: 30            moltype = DNA   length = 20
FEATURE                  Location/Qualifiers
source                   1..20
                         mol_type = other DNA
                         organism = synthetic construct
SEQUENCE: 30
taggcttcag acgcacgacc                                                  20

SEQ ID NO: 31            moltype = DNA   length = 21
FEATURE                  Location/Qualifiers
source                   1..21
                         mol_type = other DNA
                         organism = synthetic construct
SEQUENCE: 31
aagcggatgg tggttcctgc t                                                21

SEQ ID NO: 32            moltype = DNA   length = 19
FEATURE                  Location/Qualifiers
source                   1..19
                         mol_type = other DNA
                         organism = synthetic construct
SEQUENCE: 32
caccacagct cttccactc                                                   19

SEQ ID NO: 33            moltype = DNA   length = 20
FEATURE                  Location/Qualifiers
source                   1..20
```

```
                              mol_type = other DNA
                              organism = synthetic construct
SEQUENCE: 33
atcccagaac tctccgaagc                                                    20

SEQ ID NO: 34                 moltype = DNA  length = 20
FEATURE                       Location/Qualifiers
source                        1..20
                              mol_type = other DNA
                              organism = synthetic construct
SEQUENCE: 34
acccttgccg ggcaccactc                                                    20

SEQ ID NO: 35                 moltype = RNA  length = 19
FEATURE                       Location/Qualifiers
source                        1..19
                              mol_type = other RNA
                              organism = synthetic construct
SEQUENCE: 35
gcacctgccg ctttatagg                                                     19

SEQ ID NO: 36                 moltype = RNA  length = 19
FEATURE                       Location/Qualifiers
source                        1..19
                              mol_type = other RNA
                              organism = synthetic construct
SEQUENCE: 36
ccgggagtgt gcgccgctc                                                     19

SEQ ID NO: 37                 moltype = RNA  length = 19
FEATURE                       Location/Qualifiers
source                        1..19
                              mol_type = other RNA
                              organism = synthetic construct
SEQUENCE: 37
gcaactcggt ctctgggac                                                     19

SEQ ID NO: 38                 moltype = RNA  length = 19
FEATURE                       Location/Qualifiers
source                        1..19
                              mol_type = other RNA
                              organism = synthetic construct
SEQUENCE: 38
ttcgcagcgg cggcgtctc                                                     19

SEQ ID NO: 39                 moltype = RNA  length = 19
FEATURE                       Location/Qualifiers
source                        1..19
                              mol_type = other RNA
                              organism = synthetic construct
SEQUENCE: 39
acagcaccac cggcgccgg                                                     19

SEQ ID NO: 40                 moltype = RNA  length = 19
FEATURE                       Location/Qualifiers
source                        1..19
                              mol_type = other RNA
                              organism = synthetic construct
SEQUENCE: 40
caagagcgac agcaccacc                                                     19

SEQ ID NO: 41                 moltype = RNA  length = 19
FEATURE                       Location/Qualifiers
source                        1..19
                              mol_type = other RNA
                              organism = synthetic construct
SEQUENCE: 41
gagccgagta tcaagagcg                                                     19

SEQ ID NO: 42                 moltype = RNA  length = 19
FEATURE                       Location/Qualifiers
source                        1..19
                              mol_type = other RNA
                              organism = synthetic construct
SEQUENCE: 42
cctgagccga gtatcaaga                                                     19

SEQ ID NO: 43                 moltype = RNA  length = 19
FEATURE                       Location/Qualifiers
```

```
SEQ ID NO: 43              moltype = RNA  length = 19
FEATURE                    Location/Qualifiers
source                     1..19
                           mol_type = other RNA
                           organism = synthetic construct
SEQUENCE: 43
gtaggtgtca ttgaggtcc                                                19

SEQ ID NO: 44              moltype = RNA  length = 19
FEATURE                    Location/Qualifiers
source                     1..19
                           mol_type = other RNA
                           organism = synthetic construct
SEQUENCE: 44
acgcttccca gagtaggtg                                                19

SEQ ID NO: 45              moltype = RNA  length = 19
FEATURE                    Location/Qualifiers
source                     1..19
                           mol_type = other RNA
                           organism = synthetic construct
SEQUENCE: 45
cacgcttccc agagtaggt                                                19

SEQ ID NO: 46              moltype = RNA  length = 19
FEATURE                    Location/Qualifiers
source                     1..19
                           mol_type = other RNA
                           organism = synthetic construct
SEQUENCE: 46
aatggttcac gcttcccag                                                19

SEQ ID NO: 47              moltype = RNA  length = 19
FEATURE                    Location/Qualifiers
source                     1..19
                           mol_type = other RNA
                           organism = synthetic construct
SEQUENCE: 47
agaaaatggt tcacgcttc                                                19

SEQ ID NO: 48              moltype = RNA  length = 19
FEATURE                    Location/Qualifiers
source                     1..19
                           mol_type = other RNA
                           organism = synthetic construct
SEQUENCE: 48
agcactgtgg tccccagaa                                                19
```

AMPHIREGULIN GENE-SPECIFIC DOUBLE-STRANDED OLIGONUCLEOTIDE AND COMPOSITION FOR PREVENTING AND TREATING FIBROSIS-RELATED DISEASES AND RESPIRATORY DISEASES, COMPRISING SAME

CROSS-REFERENCE TO RELATED APPLICATIONS

This is a continuation under 35 U.S.C. § 120 of U.S. application Ser. No. 18/067,363, filed Dec. 16, 2022, which is a continuation under 35 U.S.C. § 120 of U.S. patent application Ser. No. 17/057,852 filed Nov. 23, 2020, which in turn is a U.S. national phase under the provisions of 35 U.S.C. § 371 of International Patent Application No. PCT/KR2019/006144 filed May 22, 2019, which in turn claims priority under 35 U.S.C. § 119 of Korean Patent Application No. 10-2018-0059783 filed May 25, 2018. The disclosures of all such applications are hereby incorporated herein by reference in their respective entireties, for all purposes.

SEQUENCE LISTING

This application includes an electronically submitted sequence listing in .XML format. The .XML file contains a sequence listing entitled 55893US_CRF_sequence-listing.xml created on Jul. 10, 2023 and is 43,336 bytes in size. The sequence listing contained in this .XML file is part of the specification and is hereby incorporated by reference herein in its entirety.

TECHNICAL FIELD

The present invention relates to a double-stranded oligonucleotide capable of very specifically inhibiting amphiregulin expression with high efficiency, preferably a double-stranded oligonucleotide comprising an RNA/RNA, DNA/DNA or DNA/RNA hybrid sequence, a double-stranded oligonucleotide structure comprising the double-stranded oligonucleotide, nanoparticle comprising the double-stranded oligonucleotide structure, and the use thereof in the prevention or treatment of fibrosis or respiratory disease.

BACKGROUND ART

In 1995, Guo and Kemphues reported that not only sense RNA but also antisense RNA is effective in inhibiting gene expression in *C. elegans*, and since then, studies have been conducted to identify the cause thereof. In 1998, Fire et al. first described the phenomenon in which injection of double-stranded RNA (dsRNA) inhibits gene expression by specifically degrading the mRNA corresponding thereto. This phenomenon was named RNA interference (RNAi). RNAi, a process that is used to inhibit gene expression, may exhibit a distinct effect of inhibiting gene expression in a simple manner at low cost, and thus the fields of application of this technology have become more diverse.

Since this technology of inhibiting gene expression may regulate the expression of a specific gene, it may remove a specific gene related to cancer, genetic disease or the like at the mRNA level, and may be used as an important tool for the development of therapeutic agents for disease treatment and validation of targets. As conventional techniques for inhibiting target gene expression, techniques of introducing a transgene for a target gene have been disclosed. These techniques include a method of introducing a transgene in the antisense direction with respect to the promoter and a method of introducing a transgene in the antisense direction with respect to the promoter.

Such RNA therapy targeting RNA is a method of removing the function of the gene of interest using oligonucleotides against the target RNA, and can be considered different from conventional methods in which therapeutic agents such as antibodies and small molecules mainly target proteins. Approaches for targeting RNA are roughly classified into two types: double-stranded-RNA mediated RNAi, and a method using an antisense oligonucleotide (ASO). Currently, clinical trials are being attempted by targeting RNA in various diseases.

An antisense oligonucleotide (hereinafter referred to as "ASO") is a short synthetic DNA designed to bind to a target gene according to Watson-Crick base pairing, and may specifically inhibit the expression of a specific nucleotide sequence of a gene. Thus, the antisense oligonucleotide has been used to study the roles of genes and to develop therapeutic agents capable of treating diseases such as cancer at the molecular level. These ASOs have the advantage of being able to be easily produced by setting various targets for inhibiting gene expression, and studies have been conducted on the use of ASOs in order to inhibit oncogene expression and cancer cell growth. A process of inhibiting the expression of a specific gene by the ASO is accomplished either by binding the ASO to a complementary mRNA sequence to induce RNase H activity and remove the mRNA or by interfering with the formation and progression of a ribosome complex for protein translation. In addition, it has been reported that the ASO binds to genomic DNA to form a triple-helix structure, thus inhibiting gene transcription. The ASO has potential as described above, but in order to use the ASO in clinical practice, it is required that the stability of the ASO against nucleases be improved and that the ASO be efficiently delivered into a target tissue or cells so as to bind specifically to the nucleotide sequence of a target gene. In addition, the secondary and tertiary structures of genetic mRNA are important factors for specific binding of the ASO, and a region in which formation of the mRNA secondary structure decreases is very advantageous for the ASO to access. Thus, efforts have been made to effectively achieve gene-specific inhibition not only in vitro but also in vivo by systematically analyzing a region in which formation of the mRNA secondary structure decreases, prior to synthesizing the ASO. These ASOs are more stable than siRNA, a kind of RNA, and have the advantage of being readily soluble in water and physiological saline. To date, three ASOs have been approved by the Federal Drug Administration (FDA) (Jessica, C., J Postdoc Res., 4:35-50, 2016).

Since the roles of RNA interference (hereinafter referred to as "RNAi") were found, it has been found that RNAi acts on sequence-specific mRNAs in various types of mammalian cells (Barik, S., J Mol. Med. (2005) 83: 764-773). When a long chain of double-stranded RNA is delivered into a cell, the delivered double-stranded RNA is converted into a small interfering RNA (hereinafter referred to as "siRNA") processed to 21 to 23 base pairs (bp) by the Dicer endonuclease. The siRNA binds to an RNA-induced silencing complex (RISC) and inhibits target gene expression in a sequence-specific manner through a process in which the guide (antisense) strand recognizes and degrades the target mRNA. Technology of inhibiting gene expression using SiRNA is used to inhibit target gene expression in target cells and to observe the resulting change, and is effectively used in studies to identify the function of a target gene in target cells. In particular, inhibiting the function of a target gene in infectious viruses or cancer cells may be effectively used to develop a treatment method for the disease of interest. As a result of conducting in vitro studies and in vivo studies using experimental animals, it has been reported that it is possible to inhibit target gene expression by siRNA.

Bertrand et al. reported that siRNA has a better inhibitory effect on mRNA expression in vitro and in vivo than an antisense oligonucleotide (ASO) for against the same target gene, and that the effect is longer lasting. In addition, regarding the mechanism of action, siRNA regulates target gene expression in a sequence-specific manner by complementary binding to the target mRNA. Thus, siRNA has an advantage over conventional antibody-based drugs or chemical drugs (small-molecule drugs) in that the range of subjects to which the siRNA is applicable can be dramatically expanded (M. A. Behlke, MOLECULAR THERAPY. 2006 13(4):664-670).

siRNA has excellent effects, and may be used in a wide range of applications, but in order for siRNA to be developed as a therapeutic agent, the in vivo stability of siRNA and the cell delivery efficiency thereof should be improved so that siRNA can be effectively delivered to cells (F. Y. Xie, Drug Discov. Today. 2006 January; 11(1-2):67-73). In order to improve in vivo stability and solve problems associated with non-specific innate immune stimulation of siRNA, studies thereon have been actively attempted by modifying some nucleotides of siRNA or the backbone thereof to have nuclease resistance, or using viral vectors, liposomes, or nanoparticles.

Delivery systems comprising a viral vector such as adenovirus or retrovirus have high transfection efficacy, but have high immunogenicity and oncogenicity. On the other hand, non-viral delivery systems containing nanoparticles have lower cell delivery efficiency than viral delivery systems, but have advantages, including high safety in vivo, target-specific delivery, efficient uptake and internalization of RNAi oligonucleotides into cells or tissues, and low cytotoxicity and immune stimulation. Thus, non-viral delivery systems are currently considered a more promising delivery method than viral delivery systems (Akhtar S, J Clin Invest. 2007 Dec. 3; 117(12): 3623-3632).

Among the non-viral delivery systems, methods that use nanocarriers are methods in which nanoparticles are formed using various polymers such as liposomes and cationic polymer complexes and in which siRNA is loaded into such nanoparticles (i.e., nanocarriers) and delivered to cells. Among the methods that use nanocarriers, frequently used methods include methods that use polymeric nanoparticles, polymer micelles, lipoplexes, and the like. Among them, lipoplexes are composed of cationic lipids, and function to interact with the anionic lipids of cellular endosomes to induce destabilization of the endosomes, thus allowing intracellular delivery of the exosomes.

In addition, it is known that the efficiency of siRNA in vivo can be increased by conjugating a chemical compound or the like to the end region of the passenger (sense) strand of the siRNA so as to impart improved pharmacokinetic characteristics thereto (J. Soutschek, Nature 11; 432(7014): 173-8, 2004). In this case, the stability of the siRNA changes depending on the properties of the chemical compound conjugated to the end of the sense (passenger) or antisense (guide) strand of the siRNA. For example, siRNA conjugated with a polymer compound such as polyethylene glycol (PEG) interacts with the anionic phosphate group of siRNA in the presence of a cationic compound to form a complex, thereby providing a carrier having improved siRNA stability (S. H. Kim, J. Control. Release 129(2):107-16, 2008). In particular, micelles composed of a polymer complex have a very small size and a very uniform size distribution compared to other drug delivery systems such as microspheres or nanoparticles, and are spontaneously formed. Thus, these micelles have advantages in that the quality of the micelle formulation is easily managed and the reproducibility thereof is easily secured.

In order to improve the intracellular delivery efficiency of siRNA, technology for ensuring the stability of the siRNA and increasing the cell membrane permeability of the siRNA using a siRNA conjugate, obtained by conjugating a hydrophilic compound (e.g., polyethylene glycol (PEG)), which is a biocompatible polymer, to the siRNA via a simple covalent bond or a linker-mediated covalent bond, has been developed (Korean Patent No. 883471). However, even when the siRNA is chemically modified and conjugated to polyethylene glycol (PEG) (PEGylation), it still has low stability in vivo and a disadvantage in that it is not easily delivered into a target organ. In order to overcome these disadvantages, a double-stranded oligo RNA structures has been developed, which comprises hydrophilic and hydrophobic compounds bound to an oligonucleotide, particularly double-stranded oligo RNA such as siRNA. This structure forms self-assembled nanoparticles, named SAMiRNA' (Self Assembled Micelle Inhibitory RNA), by hydrophobic interaction of the hydrophobic compound (Korean Patent No. 1224828). The SAMiRNA' technology has advantages over conventional delivery technologies in that homogenous nanoparticles having a very small size may be obtained.

Specifically, in the SAMiRNA' technology, PEG (polyethylene glycol) or HEG (hexaethylene glycol) is used as the hydrophilic compound. PEG, a synthetic polymer, is generally used to increase the solubility of medical drugs, particularly proteins, and to regulate the pharmacokinetics of drugs. PEG is a polydisperse material, and a one-batch polymer is made up of different numbers of monomers, and thus shows a molecular weight having a Gaussian curve. In addition, the homogeneity of a material is expressed as a polydisperse index (Mw/Mn). In other words, when PEG has a low molecular weight (3 to 5 kDa), it shows a polydisperse index of about 1.01, and when PEG has a high molecular weight (20 kDa), it shows a high a polydisperse index of about 1.2, indicating that the homogeneity of PEG decreases as the molecular weight thereof increases. Thus, when PEG is bound to a medical drug, there is a disadvantage in that the polydisperse properties of PEG are reflected to the conjugate, and thus it is not easy to verify a single material. Due to this disadvantage, processes for the synthesis and purification of PEG have been improved in order to produce materials having a low polydisperse index. However, when PEG is bound to a compound having a low molecular weight, there are problems associated with the polydisperse properties of the compound, including a problem in that it is not easy to confirm whether binding was easily achieved (Francesco M. VDRUG DISCOVERY TODAY (2005) 10(21):1451-1458).

Accordingly, in recent years, the SAMiRNA™ technology (that is self-assembled nanoparticles) has been improved by forming the hydrophilic compound of the double-stranded RNA structure (constituting SAMiRNA™) into basic unit blocks, each comprising 1 to 15 monomers having a uniform molecular weight, and if necessary, a linker, so that a suitable number of the blocks is used according to need. Thus, new types of delivery system technologies, which have small sizes and significantly improved polydisperse properties, compared to conventional SAMiRNA™, have been developed. It is already known that, when siRNA is injected, the siRNA is rapidly degraded by various enzymes present in the blood, and thus the efficiency of delivery thereof to target cells or tissues is poor. As such, variation in stability and expression inhibition rate depending on target genes also appeared in improved SAMiRNA™. Accordingly, in order to more stably and effectively inhibit the expression of a target gene using SAMiRNA™, which is composed of improved self-assembled nanoparticles, the present inventors have attempted to enhance the expression inhibitory effect on the target gene and the stability of SAMiRNA™ by applying a double-stranded oligonucleotide comprising the DNA sequence of an ASO as the guide (sense) strand and an RNA sequence as the passenger (antisense sense) sequence.

Idiopathic pulmonary fibrosis (hereinafter referred to as "IPF"), a type of fibrosis, is a disease in which chronic inflammatory cells penetrate the wall of the alveoli (pulmonary alveolus), causing various changes that make the lung stiff, lead to various severe structural changes in lung tissue, and gradually reduce the lung function, leading to death. To date, there is no effective treatment method for IPF. Once IPF symptoms appear and the patients are diagnosed with IPF, the average survival time of the patients is only about 3 to 5 years. Thus, IPF is a disease with a very poor prognosis. The incidence of IPF is reported to be about 3 to 5 per 100,000 people in foreign countries, and it is known that the incidence rate of IPF is usually higher after the 50s and is twice as high in men as in women.

Although the cause of IPF has not been clearly identified, it has been reported that the incidence of IPF is high in smokers, and antidepressants, chronic lung inhalation due to gastroesophageal reflux, chronic lung inhalation due to gastroesophageal reflux, metal dust, wood dust, solvent inhalation, and the like, are risk factors related to the occurrence of IPF. However, in most patients, no definite causal factors have been reported. As to the most frequently mentioned factor, it is known that, when Th1/Th2 reactions, coagulation cascades, etc. are activated for whatever reason, fibrotic cytokines are secreted thereby, and the activated cytokines stimulate fibroblasts and increase ECM (extracellular matrix), resulting in lung fibrosis. Of course, this process is accompanied by inflammation of the lungs, which can lead to fibrosis of the lungs, but in recent years, the opinion that this process can directly cause lung fibrosis regardless of lung inflammation is more dominant. A recent hypothesis is that pathological pulmonary fibrosis occurs during wound healing due to an abnormal signaling system in the epithelial-mesenchymal interaction. When epithelial cells are damaged, apoptosis of the epithelial cells increases, migration of the epithelial cells is restricted, differentiation of the migration of the epithelial cells is not regulated, proliferation is inhibited, and soluble factors (TGF, HGF, KGF, angiotensin II, ROS, etc.) are secreted. In addition, in this case, apoptosis of mesenchymal cells together with ECM is inhibited. Apoptosis of mesenchymal cells is inhibited, resulting in increased differentiation of myofibroblasts and causing lung fibrosis through ECM deposition, or resulting in restimulation of epithelial cells. In other words, it cannot be considered that pulmonary inflammation directly causes pulmonary fibrosis, but it means that pulmonary inflammation occurs first, and then pulmonary fibrosis occurs due to the difference between IPF patients and normal people in the process of healing to restore normal tissue. In addition, IPF can be caused by an imbalance of Th1/Th2 cytokines. A Th1 cytokine response is related to cell-mediated immunity, which restores damaged tissue areas to normal tissue, whereas Th2 cytokine causes ECM deposition and fibrosis through the activation and proliferation of fibroblasts. It has been reported that, when IFN-γ is administered to a bleomycin-induced pulmonary fibrosis model, it can prevent pulmonary fibrosis by reducing the mRNA of TGF-β and procollagen. However, since the etiology of pulmonary fibrosis is not exactly known, it is necessary to identify the initial causative factor that causes fibrosis and to develop a substance that can inhibit genes related to IPF and the TGF-β signaling system.

It is known that, when IPF is not treated, IPF continuously worsens, causing more than 50% of patients to die within 3 to 5 years. In addition, once a lung is completely hardened by fibrosis as the disease progresses, no matter what type of treatment is conducted, the patient does not improve. Therefore, it is predicted that, when IPF is treated at an early stage, the possibility of the treatment being effective will be high. A method of using a combination of a steroid with azathioprine or cyclophosphamide for IPF treatment is known, but appears to have no particular special effect. In addition, various fibrosis inhibitors have been attempted in animal experiments and in small groups of patients, but effects thereof have not been clearly demonstrated. In particular, there is no effective treatment method other than lung transplantation for patients with terminal IPF. Therefore, there is an urgent need to develop a more efficient agent for treating IPF.

Fibrosis refers to a disease condition in which a tissue or organ hardens due to excessive fibrosis of connective tissue for some reason. All processes in which fibrosis occurs follow the same path as the process in which scars are healed, regardless of area. To date, there have been few methods to cure fibrotic symptoms, and treatment methods have been developed and studied. An effective fibrosis therapeutic agent may be applied to cirrhosis, liver fibrosis, myelofibrosis, myocardial fibrosis, renal fibrosis, and pulmonary fibrosis, which are representative types of fibrosis, as well as various diseases accompanied by fibrosis, and thus there is an urgent need for an effective fibrosis therapeutic agent.

Meanwhile, it is known that amphiregulin activates the epithelial growth factor receptor (EGFR) pathway by binding to the epidermal growth factor receptor, and is involved in cell proliferation. In addition, it has been disclosed that the expression of amphiregulin can be inhibited by amphiregulin-specific siRNA, which exhibits therapeutic effects against certain types of breast cancer. In addition, it has been disclosed that the use of shRNA against amphiregulin can inhibit cell penetration in inflammatory breast cancer (Andrea Baillo, J. Cell Physiol. 2011 226(10): 2691-2701), and that when amphiregulin expression is inhibited using amphiregulin-specific shRNA, pulmonary artery remodeling in mice exposed to tobacco smoke is inhibited. It has been disclosed that amphiregulin is associated with airway smooth muscle (ASM) hyperplasia and angiogenesis, and that excessively secreted epidermal growth factor (EGF) and amphiregulin are involved, especially in promoting airway remodeling in asthmatic patients and in tissue remodeling following acute asthma.

As explained above, the possibility of amphiregulin as a therapeutic target for respiratory disease and fibrosis, particularly COPD and IPF, has been suggested, but the development of RNAi therapeutic agents for amphiregulin and technology for delivering the same is still insufficient, and the market demand for a double-stranded oligonucleotide therapeutic agent capable of inhibiting amphiregulin expression with high efficiency and specificity and technology of delivering the same is very high.

Accordingly, the present inventors selected amphiregulin as a gene associated with fibrosis including IPF, selected a double-stranded oligonucleotide that targets amphiregulin, and also identified an RNAi therapeutic agent capable of inhibiting amphiregulin expression and a carrier for delivering the same, thereby completing the present invention.

SUMMARY OF THE INVENTION

An object of the present invention is to provide a double-stranded oligonucleotide, preferably a double-stranded oligonucleotide comprising an RNA/RNA, DNA/DNA or DNA/RNA hybrid sequence, which is capable of very specifically inhibiting amphiregulin with high efficiency, a double-stranded oligonucleotide structure comprising the double-stranded oligonucleotide, and nanoparticle comprising the double-stranded oligonucleotide structure.

Another object of the present invention is to provide a pharmaceutical composition for preventing or treating fibrosis or respiratory disease comprising, as an active ingredient, the double-stranded oligonucleotide, a double-stranded oligonucleotide structure comprising the same, and/or nanoparticle comprising the double-stranded oligonucleotide structure.

Still another object of the present invention is to provide a method for preventing or treating fibrosis or respiratory disease, the method comprising a step of administering the pharmaceutical composition for preventing or treating fibrosis or respiratory disease to a subject in need of prevention or treatment of fibrosis or respiratory disease.

Yet another object of the present invention is to provide the double-stranded oligonucleotide, a double-stranded oligonucleotide structure comprising the same, and/or nanoparticle comprising the double-stranded oligonucleotide structure, for use in a method of prevention or treatment of fibrosis or respiratory disease.

Still yet another object of the present invention is to provide the pharmaceutical composition for use in a method of prevention or treatment of fibrosis or respiratory disease.

A further object of the present invention is to provide use of the double-stranded oligonucleotide, a double-stranded oligonucleotide structure comprising the same, and/or nanoparticle comprising the double-stranded oligonucleotide structure, for manufacture of a medicine for preventing fibrosis or respiratory disease.

To achieve the above objects, the present invention provides a double-stranded oligonucleotide comprising a sense strand comprising any one sequence selected from the group consisting of SEQ ID NOs: 1 to 14, more preferably the group consisting of SEQ ID NOs: 10, 11 and 12, and an antisense strand comprising a sequence complementary thereto.

The present invention also provides a double-stranded oligonucleotide structure comprising the double-stranded oligonucleotide, and nanoparticle comprising the double-stranded oligonucleotide structure.

The present invention also provides a pharmaceutical composition for preventing or treating fibrosis or respiratory disease comprising: a double-stranded oligonucleotide comprising a sense strand comprising any one sequence selected from the group consisting of SEQ ID NOs: 1 to 14, more preferably the group consisting of SEQ ID NOs: 10, 11 and 12, and an antisense strand comprising a sequence complementary thereto; or a double-stranded oligonucleotide structure comprising the double-stranded oligonucleotide; or nanoparticle comprising the double-stranded oligonucleotide structure.

The present invention also provides a method for preventing or treating fibrosis or respiratory disease, the method comprising a step of administering the pharmaceutical composition for preventing or treating fibrosis or respiratory disease to a subject in need of prevention or treatment of fibrosis or respiratory disease.

The double-stranded oligonucleotide comprising a sense strand according to the present invention, which comprises any one sequence selected from the group consisting of SEQ ID NOs: 1 to 14, more preferably the group consisting of SEQ ID NOs: 10, 11 and 12, and an antisense strand comprising a sequence complementary thereto, or a double-stranded oligonucleotide structure comprising the double-stranded oligonucleotide, or nanoparticle comprising the double-stranded oligonucleotide structure may very efficiently inhibit amphiregulin expression, and thus each of the double-stranded oligonucleotide according to the present invention, a double-stranded oligonucleotide structure comprising the same, and nanostructures comprising the double-stranded oligonucleotide structure may be effectively used for the prevention or treatment of fibrosis or respiratory disease.

The sequence of SEQ ID NO: 10, 11 and 12 which is comprised in a preferred double-stranded oligonucleotide provided to achieve the above object is as follows:

```
                                        (SEQ ID NO: 10)
        5'-CACCTACTCTGGGAAGCGT-3'

(SEQ ID NO: 11)
        5'-ACCTACTCTGGGAAGCGTG-3'

(SEQ ID NO: 12)
        5'-CTGGGAAGCGTGAACCATT-3'
```

As used herein, the term "double-stranded oligonucleotide" is intended to include all materials having general RNAi (RNA interference) activity, and it will be obvious to those skilled in the art that an mRNA-specific double-stranded oligonucleotide that encodes the amphiregulin protein also includes amphiregulin-specific shRNA and the like. That is, the oligonucleotide may be siRNA, shRNA or miRNA.

In addition, it will be obvious to those skilled in the art that amphiregulin-specific siRNA which comprises a sense strand and an antisense strand, or an antisense oligonucleotide, each comprising a sequence resulting from substitution, deletion or insertion of one or more nucleotides in a sense strand comprising any one sequence selected from the group consisting of SEQ ID NOs: 10, 11 and 12, or an antisense strand complementary thereto, is also included in the scope of the present invention, as long as the specificity for amphiregulin is maintained.

In the present invention, the sense or antisense strand may be independently DNA or RNA. In addition, the sense and antisense strands may be in the form of a hybrid in which the sense strand is DNA and the antisense strand is RNA or the sense strand is RNA and the antisense strand is DNA.

In the present invention, SEQ ID NOs: 10, 11 and 12 are set forth in the form of DNA, but when the form of RNA is used, the sequences of SEQ ID NOs: 10, 11 and 12 may be RNA sequences corresponding thereto, that is, sequences in which T is substituted with U.

In addition, the double-stranded oligonucleotide according to the present invention includes not only the case where the sense strand of the sequence is fully complementary (perfect match) to the binding site of the amphiregulin gene, but also the case where the sense strand is partially complementary (mismatch) to the binding site, as long as the specificity for amphiregulin is maintained.

The double-stranded oligonucleotide according to the present invention may comprise, at the 3' end of one or both strands, an overhang comprising one or more unpaired nucleotides.

In the present invention, the sense strand or the antisense strand may preferably consist of 19 to 31 nucleotides, but is not limited thereto.

In the present invention, the double-stranded oligonucleotide comprising the sense strand, comprising any one sequence selected from the group consisting of SEQ ID NOs: 10, 11 and 12, and the antisense strand comprising a sequence complementary thereto, may be specific for amphiregulin, but is not limited thereto.

In the present invention, the sense strand or antisense strand of the double-stranded oligonucleotide may comprise various chemical modifications in order to increase the in vivo stability thereof or impart nuclease resistance and reduce non-specific immune responses. The chemical modification may be one or more selected from, without limitation to, the group consisting of the following chemical modifications: modification in which an OH group at the 2' carbon position of a sugar structure in one or more nucleotides is substituted with any one selected from the group consisting of —CH$_3$ (methyl), —OCH$_3$ (methoxy), amine (—NH$_2$), fluorine (—F), —O-2-methoxyethyl, —O-propyl, —O-2-methylthioethyl, —O-3-aminopropyl, —O-3-dimethylaminopropyl, —O—N-methylacetamido and —O-dimethylamidooxyethyl; modification in which oxygen in a sugar structure in nucleotides is substituted with sulfur; modification of a bond between nucleotides to any one bond selected from the group consisting of a phosphorothioate bond, a boranophosphophate bond and a methyl phosphonate bond; modification to PNA (peptide nucleic acid), LNA (locked nucleic acid) or UNA (unlocked nucleic acid); and modification to a DNA-RNA hybrid (*Ann. Rev. Med.* 55, 61-65 2004; U.S. Pat. Nos. 5,660,985; 5,958,691; 6,531,584; 5,808,023; 6,326,358; 6,175,001; *Bioorg. Med. Chem. Lett.* 14:1139-1143, 2003; *RNA*, 9:1034-1048, 2003; *Nucleic Acid Res.* 31:589-595, 2003; *Nucleic Acids Research*, 38(17) 5761-773, 2010; *Nucleic Acids Research*, 39(5):1823-1832, 2011).

In the present invention, one or more phosphate groups, preferably one to three phosphate groups, may be bound to the 5' end of the antisense strand of the double-stranded oligonucleotide.

In another aspect, the present invention is directed to a double-stranded oligonucleotide structure comprising a structure represented by the following Formula (1), wherein A represents a hydrophilic compound, B represents a hydrophobic compound, X and Y each independently represent a simple covalent bond or a linker-mediated covalent bond, and R represents a double-stranded oligonucleotide.

In a preferred embodiment, the double-stranded oligonucleotide structure comprising an amphiregulin-specific sequence according to the present invention preferably has a structure represented by the following Structural Formula (1):

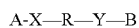   Structural Formula (1)

wherein A represents a hydrophilic compound, B represents a hydrophobic compound, X and Y each independently represent a simple covalent bond or a linker-mediated covalent bond, and R represents a double-stranded oligonucleotide.

The double-stranded oligonucleotide according to the present invention is preferably in the form of a DNA-RNA hybrid, siRNA (short interfering RNA), shRNA (short hairpin RNA) or miRNA (microRNA), but is not limited thereto, and may also include a single-stranded miRNA inhibitor that may act as an antagonist against miRNA.

Hereinafter, the double-stranded oligonucleotide according to the present invention will be described with a focus on RNA, but it is will be obvious to those skilled in the art that the present invention may also be applied to other double-stranded oligonucleotides having the same characteristics as the double-stranded oligonucleotide of the present invention.

More preferably, the double-stranded oligonucleotide structure comprising the amphiregulin-specific double-stranded oligonucleotide according to the present invention has a structure represented by the following Structural Formula (2):

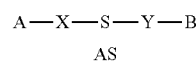   Structural Formula (2)

wherein A, B, X and Y are as defined in Structural Formula (1) above, S represents the sense strand of the amphiregulin-specific double-stranded oligonucleotide, and AS represents the antisense strand of the amphiregulin-specific double-stranded oligonucleotide.

More preferably, the double-stranded oligonucleotide structure comprising the amphiregulin-specific double-stranded oligonucleotide has a structure represented by the following Structural Formula (3) or (4):

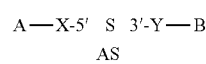   Structural Formula (3)

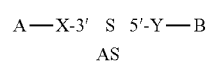   Structural Formula (4)

wherein A, B, S, AS, X and Y are as defined in Structural Formula (2) above, and 5' and 3' represent the 5' end and 3' end, respectively, of the sense strand of the amphiregulin-specific double-stranded oligonucleotide.

The hydrophilic compound may be selected from the group consisting of polyethylene glycol (PEG), polyvinylpyrrolidone, and polyoxazoline, but is not limited thereto.

It will be obvious to those skilled in the technical field to which the present invention pertains that one to three phosphate groups may be bound to the 5' end of the antisense strand of the double-stranded oligonucleotide RNA structure comprising the amphiregulin-specific siRNA as shown in Structural Formula (1) to Structural Formula (4) and that shRNA may be used in place of the RNA.

The hydrophilic compound in Structural Formula (1) to Structural Formula (4) above is preferably a polymer compound having a molecular weight of 200 to 10,000, more preferably a polymer compound having a molecular weight of 1,000 to 2,000. For example, as the hydrophilic polymer compound, it is preferable to use a nonionic hydrophilic polymer compound such as polyethylene glycol, polyvinyl pyrrolidone or polyoxazoline, but the disclosure is not limited thereto.

In particular, the hydrophilic compound (A) in Structural Formula (1) to Structural Formula (4) may be used in the form of hydrophilic blocks as shown in the following Structural Formula (5) or (6), and a suitable number (n in Structural Formula (5) or (6)) of such hydrophilic blocks may be used as required, thereby overcoming the problems associated with polydisperse properties that may occur when general synthetic polymer compounds are used:

(A'$_m$-J)$_n$  Structural Formula (5)

(J-A'$_m$)$_n$  Structural Formula (6)

wherein A' represents a hydrophilic monomer, J represents a linker that connects a number (m) of hydrophilic monomers together or connects a number (m) of hydrophilic monomers with the double-stranded oligonucleotide, m is an integer ranging from 1 to 15, n is an integer ranging from 1 to 10, and a repeat unit represented by (A'$_n$-J) or (J-A$_n$') corresponds to the basic unit of the hydrophilic block.

When the hydrophilic block as shown in Structural Formula (5) or (6) above is used, the double-stranded oligonucleotide structure comprising the amphiregulin-specific oligonucleotide according to the present invention may have a structure represented by the following Structural Formula (7) or (8):

(A'$_m$-J)$_n$-X—R—Y—B  Structural Formula (7)

(J-A'$_m$)$_n$-X—R—Y—B  Structural Formula (8)

wherein X, R, Y and B are as defined in Structural Formula (1) above, and A', J, m and n are as defined in Structural Formulas (5) and (6) above.

As the hydrophilic monomer (A') in Structural Formulas (5) and (6) above, one selected from among nonionic hydrophilic polymers may be used without limitation, as long as it is compatible with the purpose of the present invention. Preferably, a monomer selected from among compound (1) to compound (3) set forth in Table 1 below may be used. More preferably, a monomer of compound (1) may be used. In compound (1), G may preferably be selected from among O, S and NH.

In particular, among hydrophilic monomers, the monomer represented by compound (1) is very suitable for the production of the structure according to the present invention, because the monomer has advantages in that various functional groups may be introduced to the monomer, and the monomer induces little immune response by having good in vivo affinity and excellent biocompatibility, may increase the in vivo stability of the double-stranded oligonucleotide comprised in the structure represented by Structural Formula (7) or (8), and may increase the delivery efficiency of the double-stranded oligonucleotide.

TABLE 1

Structure of hydrophilic monomers used in the present invention

| Compound (1) | Compound (2) | Compound (3) |
|---|---|---|
|  | 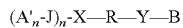 | 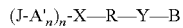 |
|  | | |
| G is O, S or NH | | |

The total molecular weight of the hydrophilic compound in Structural Formula (5) to Structural Formula (8) is preferably in the range of 1,000 to 2,000. Thus, for example, when compound (1) in Structural Formula (7) and Structural Formula (8) is hexaethylene glycol, that is, a compound in which G is O and m is 6, the repeat number (n) is preferably 3 to 5, because the hexaethylene glycol space has a molecular weight of 344. Particularly, the present invention is characterized in that a suitable number (represented by n) of repeat units of the hydrophilic group (hydrophilic blocks) represented by (A'$_m$-J) or (J-A'$_n$)$_n$ in Structural Formula (5) and Structural Formula (6) may be used as required. The hydrophilic monomer J and linker J comprised in each hydrophilic block may be the same or different between the hydrophilic blocks. In other words, when 3 hydrophilic blocks are used (n=3), the hydrophilic monomer of compound (1), the hydrophilic monomer of compound (2) and the hydrophilic monomer of compound (3) may be used in the first, second and third blocks, respectively, suggesting that different monomers may be used in all hydrophilic blocks. Alternatively, any one hydrophilic monomer selected from the hydrophilic monomers of compounds (1) to (3) may also be used in all of the hydrophilic blocks. Similarly, as the linker that mediates the bonding of the hydrophilic monomer, the same linker may be used in the hydrophilic blocks, or different linkers may also be used in the hydrophilic blocks. In addition, m, which is the number of hydrophilic monomers, may also be the same or different between the hydrophilic blocks. In other words, in the first hydrophilic block, three hydrophilic monomers are connected (m=3), in the second hydrophilic block, five hydrophilic monomers are connected (m=5), and in the third hydrophilic block, four hydrophilic monomers are connected (m=4), suggesting that different numbers of hydrophilic monomers may be used in the hydrophilic blocks. Alternatively, the same number of hydrophilic monomers may also be used in all hydrophilic blocks.

In addition, in the present invention, the linker (J) is preferably selected from the group consisting of —PO$_3^-$—, —SO$_3$— and —CO$_2$—, but is not limited thereto. It will be obvious to those skilled in the art that any linker selected in consideration of the hydrophilic monomer that is used may be used, as long as it is compatible with the purpose of the present invention.

The hydrophobic compound (B) in Structural Formula (1) to Structural Formula (4), Structural Formula (7) and Structural Formula (8) functions to form nanoparticles composed of the oligonucleotide structure shown in Structural Formula (1) to Structural Formula (4), Structural Formula (7) and Structural formula (8) through hydrophobic interactions. The hydrophobic compound preferably has a molecular weight of 250 to 1,000, and may be any one selected from the group consisting of a steroid derivative, a glyceride derivative, glycerol ether, polypropylene glycol, a C$_{12}$-C$_{50}$ unsaturated or saturated hydrocarbon, diacylphosphatidylcholine, a fatty acid, a phospholipid, lipopolyamine, a lipid, tocopherol, and tocotrienol, but is not limited thereto. It will be obvious to those skilled in the art that any hydrophobic compound may be used, as long as it is compatible with the purpose of the present invention.

The steroid derivative may be selected from the group consisting of cholesterol, cholestanol, cholic acid, cholesteryl formate, cholestanyl formate, and cholesteryl amine, and the glyceride derivative may be selected from among mono-, di-, and tri-glycerides and the like. Here, the fatty acid of the glyceride is preferably a C$_{12}$-C$_{50}$ unsaturated or saturated fatty acid.

In particular, among the hydrophobic compounds, a saturated or unsaturated hydrocarbon or cholesterol is preferably used because it may be easily bound in a step of synthesizing the double-stranded oligonucleotide structure according to the present invention. Most preferably, a $C_{24}$ hydrocarbon, particularly a hydrophobic hydrocarbon containing a disulfide bond, is used.

The hydrophobic compound may be bound to the distal end of the hydrophilic compound, and may be bound to any position on the sense or antisense strand of the double-stranded oligonucleotide.

The hydrophilic compound or hydrophobic compound in Structural Formulas (1) to (4), (7) and (8) according to the present invention is bound to the amphiregulin-specific oligonucleotide by a single covalent bond or a linker-mediated covalent bond (X or Y). The linker that mediates the covalent bond is covalently bound to the hydrophilic or hydrophobic compound at the end of the amphiregulin-specific oligonucleotide, and is not specifically limited, as long as it provides a degradable bond in a specific environment if required. Therefore, the linker that is used in the present invention may be any compound that is bound in order to activate the amphiregulin oligonucleotide and/or the hydrophilic (or hydrophobic) compound in the process of producing the double-stranded oligonucleotide structure according to the present invention. The covalent bond may be either one of a non-degradable bond and a degradable bond. Here, examples of the non-degradable bond include, but are not limited to, an amide bond and a phosphate bond, and examples of the degradable bond include, but are not limited to, a disulfide bond, an acid-degradable bond, an ester bond, an anhydride bond, a biodegradable bond, and an enzyme-degradable bond.

In addition, as the amphiregulin-specific double-stranded oligonucleotide represented by R (or S and AS) in Structural Formulas (1) to (4), (7) and (8), any double-stranded oligonucleotide having the property of binding specifically to the mRNA of amphiregulin may be used without limitation. Preferably, the amphiregulin-specific double-stranded oligonucleotide according to the present invention comprises a sense strand comprising any one sequence selected from among SEQ ID NOs: 10, 11 and 12, and an antisense strand comprising a sequence complementary to that of the sense strand.

In addition, in the double-stranded oligonucleotide structure comprising the amphiregulin-specific double-stranded oligonucleotide according to the present invention, an amine or polyhistidine group may additionally be introduced to the distal end of the hydrophilic compound bound to the oligonucleotide in the structure.

This facilitates the intracellular uptake and endosomal escape of a carrier comprising the double-stranded oligonucleotide structure comprising the amphiregulin-specific double-stranded oligonucleotide according to the present invention, and it has already been reported that the introduction of an amine group and a polyhistidine group may be used to facilitate the intracellular uptake and endosomal escape of carriers such as quantum dots, dendrimers or liposomes.

Specifically, it is known that a primary amine group introduced to the end or outside of a carrier is protonated at biological pH while forming a conjugate by interaction with a negatively charged gene, and that endosomal escape is facilitated due to an internal tertiary amine having a buffering effect at low pH after intracellular uptake, whereby the carrier can be protected from lysosomal degradation (Gene Delivery and Expression Inhibition Using Polymer-Based Hybrid Material, *Polymer Sci. Technol.*, Vol. 23, No. 3, pp 254-259).

In addition, it is known that histidine, a non-essential amino acid, has an imidazole ring (pKa=6.04) at the residue (—R) thereof, and thus has an effect of increasing buffering capacity in endosomes and lysosomes, and thus histidine modification may be used in non-viral gene carriers, including liposomes, in order to increase endosomal escape efficiency (Novel histidine-conjugated galactosylated cationic liposomes for efficient hepatocyte selective gene transfer in human hepatoma HepG2 cells. J. Controlled Release 118, pp 262-270).

The amine group or polyhistidine group may be connected to the hydrophilic compound or the hydrophilic block by one or more linkers.

When the amine group or polyhistidine group is introduced to the hydrophilic compound of the double-stranded oligonucleotide structure represented by Structural Formula (1) according to the present invention, the RNA structure may have a structure shown in the following Structural Formula (9):

P-J$_1$-J$_2$-A-X—R—Y—B        Structural Formula (9)

wherein A, B, R, X and Y are as defined in Structural Formula (1) above,

P represents an amine group or a polyhistidine group, and J$_1$ and J$_2$ are linkers each of which may be independently selected from among a simple covalent bond, PO$_3^-$, SO$_3$, CO$_2$, a C$_{2-12}$ alkyl, alkenyl and alkynyl, but without limitation thereto. It will be obvious to those skilled in the art that any linkers selected in consideration of the hydrophilic compound used herein may be used as J$_1$ and J$_2$, as long as they are compatible with the purpose of the present invention.

Preferably, when an amine group is introduced, J$_2$ is a simple covalent bond or PO$_3^-$, and J$_1$ is a C$_6$ alkyl, but the present invention is not limited thereto.

In addition, when a polyhistidine group is introduced, it is preferred that J$_2$ in Structural Formula (9) be a simple covalent bond or PO$_3^-$, and that J$_1$ be compound (4), but the present invention is not limited thereto.

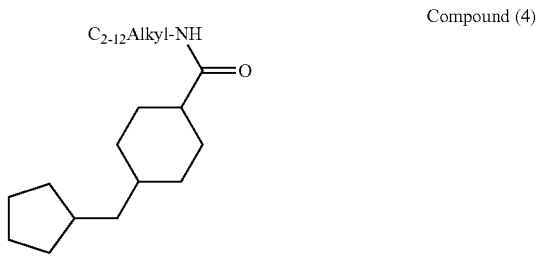

Compound (4)

In addition, when the hydrophilic compound of the double-stranded oligonucleotide structure shown in Structural Formula (9) is the hydrophilic block represented by Structural Formula (5) or (6) and an amine group or a polyhistidine group is introduced thereto, the double-stranded oligonucleotide structure may have a structure represented by the following Structural Formula (10) or (11):

P-J$_1$-J$_2$-(A'$_m$-J)$_n$-X—R—Y—B        Structural Formula (10)

P-J$_1$-J$_2$-(J-A'$_m$)$_n$-X—R—Y—B        Structural Formula (11)

wherein X, R, Y, B, A', J, m and n are as defined in Structural Formula (5) or (6) above, and P, $J_1$ and $J_2$ are as defined in Structural Formula (9).

In particular, the hydrophilic compound in Structural Formula (10) and Structural Formula (11) is preferably bound to the 3' end of the sense strand of the amphiregulin-specific double-stranded oligonucleotide. In this case, Structural Formula (9) to Structural Formula (11) may correspond to the following Structural Formula (12) to Structural Formula (14):

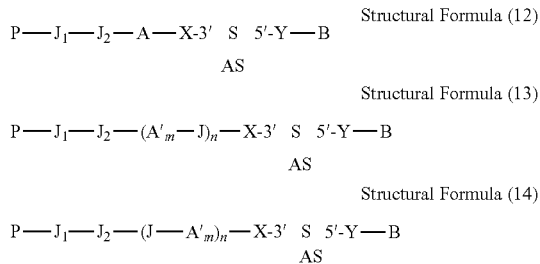

wherein X, R, Y, B, A, A' J, m, n, P, $J_1$ and $J_2$ are as defined in Structural Formula (9) to Structural Formula (11) above, and 5' and 3' represent the 5' end and the 3' end of the sense strand of the amphiregulin-specific double-stranded oligonucleotide.

An amine group that may be introduced in the present invention may be a primary, secondary or tertiary amine group. In particular, a primary amine group is preferably used. The introduced amine group may be present as an amine salt. For example, a salt of the primary amine group may be present as $NH_3^+$.

In addition, a polyhistidine group that may be introduced in the present invention preferably comprises 3 to 10 histidines, more preferably 5 to 8 histidines, and most preferably six histidines. In addition to histidines, one or more cysteines may be included.

Meanwhile, when a targeting moiety is provided in the double-stranded oligonucleotide structure comprising the amphiregulin-specific oligonucleotide according to the present invention and nanoparticles formed therefrom, it may promote the efficient delivery of the RNA structure to target cells so that the RNA structure may be delivered to the target cells even at a relatively low concentration, thus exhibiting a strong effect of regulating target gene expression. In addition, the targeting moiety may prevent non-specific delivery of the amphiregulin-specific double-stranded oligonucleotide to other organs and cells.

Accordingly, the present invention provides a double-stranded oligo RNA structure in which a ligand (L), particularly a ligand having the property of binding specifically to a receptor that enhances target cell internalization by receptor-mediated endocytosis (RME), is further bound to the structure represented by any one of Structural Formulas (1) to (4), (7) and (8). For example, a structure wherein a ligand is bound to the double-stranded oligo RNA structure represented by Structural Formula (1) has a structure shown in the following Structural Formula (15):

(L$_i$-Z)-A-X—R—Y—B    Structural Formula (15)

wherein A, B, X and Y are as defined in Structural Formula (1) above, L is a ligand having the property of binding specifically to a receptor that enhances target cell internalization by receptor-mediated endocytosis (RME), and "i" is an integer ranging from 1 to 5, preferably from 1 to 3.

The ligand in Structural Formula (15) may preferably be selected from among: target receptor-specific antibodies, aptamers and peptides, which have the RME property of enhancing target cell internalization; folate (the term "folate" is generally used interchangeably with folic acid, and the term "folate" as used herein means folate that is in a natural form or is activated in the human body); and chemical compounds, including hexosamines such as N-acetyl galactosamine (NAG), and sugars or carbohydrates such as glucose and mannose, but is not limited thereto.

In addition, the hydrophilic compound (A) in Structural Formula (15) above may be used in the form of the hydrophilic block represented by Structural Formula (5) or (6).

In another aspect, the present invention provides a method for producing a double-stranded oligonucleotide structure comprising an amphiregulin-specific double-stranded oligonucleotide.

For example, the method for producing a double-stranded oligonucleotide structure comprising an amphiregulin-specific double-stranded oligonucleotide according to the present invention may comprise steps of:

(1) binding a hydrophilic compound to a solid support;
(2) synthesizing an oligonucleotide single strand on the hydrophilic compound-bound solid support;
(3) covalently binding a hydrophobic compound to the 5' end of the oligonucleotide single strand;
(4) synthesizing an oligonucleotide single strand having a sequence complementary to the sequence of the oligonucleotide single strand of step (2);
(5) separating and purifying an oligonucleotide-polymer structure and the oligonucleotide single strand from the solid support after completion of synthesis; and
(6) annealing the produced oligonucleotide-polymer structure with the oligonucleotide single strand having the complementary sequence, thereby producing a double-stranded oligonucleotide structure.

The solid support that is used in the present invention is preferably controlled pore glass (CPG), but is not limited thereto, and polystyrene (PS), polymethylmethacrylate (PMMA), silica gel, cellulose paper or the like may also be used. When CPG is used, it preferably has a diameter of 40 to 180 μm and a pore size of 500 to 3,000 Å. After step (5), the molecular weights of the produced and purified RNA-polymer structure and oligonucleotide single strand may be measured using a MALDI-TOF mass spectrometer in order to confirm that the desired oligonucleotide-polymer structure and oligonucleotide single strand are obtained. In the above-described production method, step (4) of synthesizing the oligonucleotide single strand having a sequence complementary to the sequence of the oligonucleotide single strand synthesized in step (2) may be performed before step (1) or during any one step of steps (1) to (5).

In addition, the oligonucleotide single strand having a sequence complementary to the sequence of the oligonucleotide single strand synthesized in step (2) may be used in the state in which a phosphate group is bound to the 5' end of the oligonucleotide single strand.

Meanwhile, the present invention provides a method for producing a double-stranded oligonucleotide structure wherein a ligand is further bound to the double-stranded oligonucleotide structure comprising the amphiregulin-specific double-stranded oligonucleotide.

For example, the method for producing the ligand-bound double-stranded oligonucleotide structure comprising the amphiregulin-specific double-stranded oligonucleotide may comprise steps of:

(1) binding a hydrophilic compound to a solid support having a functional group bound thereto;
(2) synthesizing an oligonucleotide single strand on the solid support having the functional group and hydrophilic compound bound thereto;
(3) covalently binding a hydrophobic compound to the 5' end of the oligonucleotide single strand;
(4) synthesizing an oligonucleotide single strand having a sequence complementary to the sequence of the oligonucleotide single strand synthesized in step (2);
(5) separating the functional group-oligonucleotide-polymer structure and the oligonucleotide single strand having the complementary sequence from the solid support after completion of synthesis;
(6) binding a ligand to the end of the hydrophilic compound by the functional group to produce a ligand-oligonucleotide-polymer structure single strand; and
(7) annealing the produced ligand-oligonucleotide-polymer structure with the oligonucleotide single strand having the complementary sequence, thereby producing a ligand/double-stranded-oligonucleotide structure.

After step (6), the produced ligand-oligonucleotide-polymer structure and the oligonucleotide single strand having the complementary sequence may be separated and purified, and then the molecular weights thereof may be measured using a MALDI-TOF mass spectrometer in order to confirm that the desired ligand-RNA-polymer structure and the desired RNA single strand having the complementary sequence are produced. By annealing the produced ligand/RNA-oligonucleotide structure with the oligonucleotide single strand having the complementary sequence, a ligand/double-stranded-oligonucleotide structure may be produced. In the above-described production method, step (4) of synthesizing the oligonucleotide single strand having a sequence complementary to the sequence of the oligonucleotide single strand synthesized in step (3) may be performed before step (1) or during any one step of steps (1) to (6).

In still another aspect, the present invention is directed to nanoparticles comprising the double-stranded oligonucleotide structure according to the present invention. The double-stranded oligonucleotide according to the present invention forms self-assembled nanoparticles through hydrophobic interaction of the hydrophobic compound (Korean Patent No. 1224828). These nanoparticles have excellent in vivo delivery efficiency and in vivo stability. In addition, the high particle size uniformity of the nanoparticles makes quality control (QC) easy, and thus a process of preparing these nanoparticles as a drug is easy.

In the present invention, the nanoparticle may also be composed of a mixture of double-stranded oligonucleotide structures comprising double-stranded structures comprising different sequences. For example, the nanoparticle may comprise one kind of amphiregulin-specific double-stranded oligonucleotide comprising a sense strand, which comprises any one sequence selected from SEQ ID NOs: 10 to 12, and an antisense strand comprising a sequence complementary thereto; however, in another embodiment, the nanoparticle may comprise different kinds of amphiregulin-specific double-stranded oligonucleotides, each comprising a sense strand, which comprises any one sequence selected from SEQ ID NOs: 10 to 12, and an antisense strand comprising a sequence complementary thereto, and may also comprise an amphiregulin-specific double-stranded oligonucleotide which is not disclosed in the present invention.

In still another aspect, the present invention is directed to a pharmaceutical composition for preventing or treating fibrosis or respiratory disease, the pharmaceutical composition containing, as an active ingredient, the double-stranded oligonucleotide according to the present invention, the double-stranded oligonucleotide structure, or nanoparticle comprising the double-stranded oligonucleotide structure.

The pharmaceutical composition for preventing or treating fibrosis or respiratory disease according to the present invention exhibits effects on the prevention or treatment of fibrosis or respiratory disease by inhibiting connective tissue remodeling, particularly pulmonary artery remodeling and airway remodeling.

In the present invention, the respiratory disease may be chronic obstructive disease (COPD), asthma, acute and chronic bronchitis, allergic rhinitis, cough, sputum, bronchitis, bronchiolitis, sore throat, tonsillitis, or laryngitis, and the fibrosis may be selected from the group consisting of idiopathic pulmonary fibrosis (IPF), liver fibrosis, cirrhosis, myelofibrosis, myocardial fibrosis, renal fibrosis, pulmonary fibrosis, cardiac fibrosis, and radiation-induced fibrosis, but the present invention is not limited thereto. In the present invention, the radiation-induced fibrosis is a side effect that is frequently caused by radiotherapy commonly used for the treatment of cancer, tumors, etc., and the term "radiation-induced fibrosis" may be used interchangeably with the term "radiation fibrosis syndrome (RFS)".

For administration, the composition of the present invention may further contain one or more pharmaceutically acceptable carriers, in addition to the above-described active ingredient. The pharmaceutically acceptable carriers should be compatible with the active ingredient, and may be selected from among physiological saline, sterile water, Ringer's solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, a diluent, a dispersing agent, a surfactant, a binder and a lubricant may additionally be added to the composition to prepare injectable formulations such as an aqueous solution, a suspension, and an emulsion. In particular, the composition is preferably provided as a lyophilized formulation. For the preparation of a lyophilized formulation, a conventional method known in the technical field to which the present invention pertains may be used, and a stabilizer for lyophilization may also be added. Furthermore, the composition may preferably be formulated according to each disease or components by a suitable method known in the art or by a method disclosed in Remington's Pharmaceutical Science, Mack Publishing Company, Easton PA.

The dose of the composition of the present invention may be determined by a person skilled in the art based on the condition of the patient and the severity of the disease. In addition, the composition may be formulated in various dosage forms, including powders, tablets, capsules, liquids, injectable solutions, ointments and syrup formulations, and may be provided in unit-dosage or multi-dosage containers, for example, sealed ampules or vials.

The composition of the present invention may be administered orally or parenterally. The composition according to the present invention may be administered, for example, orally, via inhalation, intravenously, intramuscularly, intraarterially, intramedullarily, intradurally, intracardially, transdermally, subcutaneously, intraperitoneally, intrarectally, sublingually, or topically, but is not limited thereto. In particular, the composition may also be administered into the lungs by intrabronchial instillation for the treatment of respiratory disease. The dose of the composition according to the present invention may vary depending on the patient's weight, age, sex, state of health and diet, the duration of administration, the mode of administration, excretion rate, severity of disease, or the like, and may be easily determined by those skilled in the art. In addition, for clinical administration, the composition of the present invention may be prepared into a suitable formulation using a known technique.

In another aspect, the present invention is directed to a lyophilized formulation comprising the pharmaceutical composition according to the present invention.

In still another aspect, the present invention is directed to a method for preventing or treating fibrosis or respiratory disease, the method comprising a step of administering the pharmaceutical composition for preventing or treating fibrosis or respiratory disease according to the present invention to a subject in need of prevention or treatment of fibrosis or respiratory disease.

In the present invention, the respiratory disease may be chronic obstructive disease (COPD), asthma, acute and chronic bronchitis, allergic rhinitis, cough, sputum, bronchitis, bronchiolitis, sore throat, tonsillitis, or laryngitis, and the fibrosis may be selected from the group consisting of idiopathic pulmonary fibrosis (IPF), liver fibrosis, cirrhosis, myelofibrosis, myocardial fibrosis, renal fibrosis, pulmonary fibrosis, cardiac fibrosis, and radiation-induced fibrosis, but the present invention is not limited thereto.

In yet another aspect, the present invention is directed to provide the double-stranded oligonucleotide, a double-stranded oligonucleotide structure comprising the same, and nanoparticle comprising the double-stranded oligonucleotide structure, for use in a method of the prevention or treatment of fibrosis or respiratory disease.

In still yet another aspect, the present invention is directed to a pharmaceutical composition for use in a method of the prevention or treatment of fibrosis or respiratory disease.

In a further aspect, the present invention is directed to the use of the double-stranded oligonucleotide, a double-stranded oligonucleotide structure comprising the same, and nanoparticle comprising the double-stranded oligonucleotide structure, for the manufacture of a medicine for preventing fibrosis or respiratory disease.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A: SAMi-AREG #10, FIG. 2B: SAMi-AREG #11, and FIG. 2C: SAMi-AREG #12.

FIG. 7A: DNA/RNA hybrid SAMiRNA, and FIG. 7B: RNA/RNA hybrid SAMiRNA.

FIG. 8 is a graph comparing the mRNA expression levels of amphiregulin in the lung cancer cell line A549 treated with different concentrations (200 nM, 600 nM and 1,200 nM) of SAMiRNA having each of the sequences of SEQ ID NOs: 10 (AR-1), 11 (AR-2) and 12 (AR-3) of the present invention as a sense strand.

DETAILED DESCRIPTION AND PREFERRED EMBODIMENTS OF THE INVENTION

Figure 1:
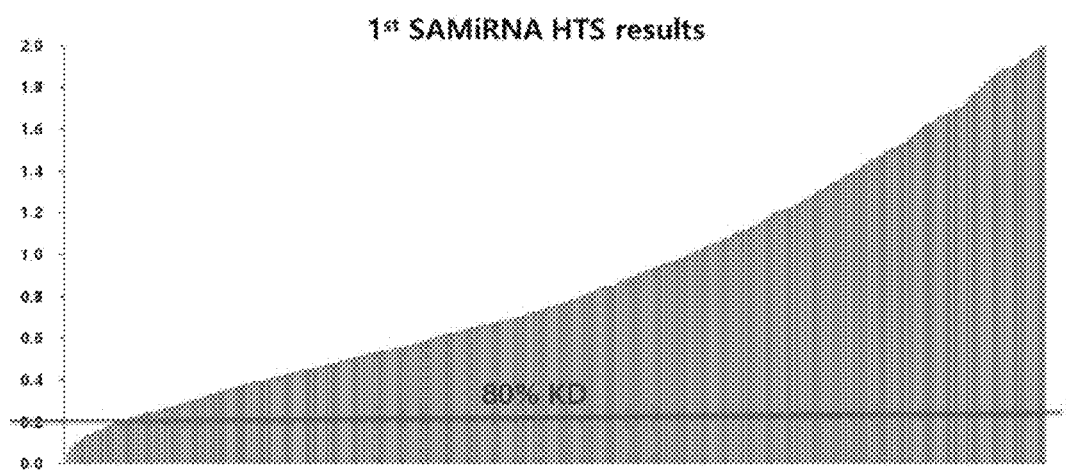
FIG. 1 shows the results of screening 1,257 SAMiRNAs targeting human amphiregulin.

Hereinafter, the present invention will be described in more detail with reference to examples. It will be obvious to those skilled in the art that these examples are only to explain the present invention in more detail and the scope of the present invention is not limited by these examples. Thus, the substantial scope of the present invention will be defined by the appended claims and equivalents thereto.

In the present invention, three specific sequences capable of inhibiting amphiregulin expression were identified, and it was confirmed that these sequences can bind complementarily to an mRNA encoding amphiregulin and effectively inhibit amphiregulin expression, thereby effectively treating fibrosis and respiratory diseases.

Example 1. Algorithm for Screening of SAMiRNAs Targeting Amphiregulin and Selection of Candidate Sequences SAMiRNA-based drug high-throughput screening is a method in which all possible candidate sequences are generated by applying a 1-base or 2-base sliding window algorithm to the entire mRNA, unnecessary candidate sequences are removed by performing homology filtering, and the degrees to which the expression of the gene of interest is inhibited by all the finally selected SAMiRNAs are determined.

First, a design process for SAMiRNA candidate sequences against amphiregulin was performed. Specifically, 1,257 SAMiRNA candidate sequences, each consisting of 19 nucleotides, were selected by applying a 1-base sliding window algorithm to the human amphiregulin mRNA NM 001657.3 (1,290 bp), and an experiment on the degree of inhibition of amphiregulin was performed.

Example 2. Synthesis of Double-Stranded Oligo RNA Structure

A double-stranded oligo RNA structure (SAMiRNA) produced in the present invention is represented by the following structural formula:

$C_{24}$-5'S 3'-(hexaethyleneglycol-$PO_4^-$)$_3$-hexaethyleneglycol

AS 5'-PO4

For synthesis of the sense strain of a monoSAMiRNA (n=4) double-stranded oligo structure, 3,4,6-triacetyl-1-hexa(ethylene glycol)-N-acetyl galactosamine-CPG was used as a support, and three demethoxytrityl (DMT) hexaethylene glycol phosphoramidates as hydrophilic monomers were continuously bound to the support through a reaction. Next, synthesis of RNA or DNA was performed, and then hydrophobic $C_{24}$ ($C_6$—S—S—$C_{18}$) containing a disulfide bond was bound to the 5' end region, thereby synthesizing the sense strand of monoSAMiRNA (n=4) in which NAG-hexaethyleneglycol-(—$PO_3^-$ hexaethyleneglycol)$_3$ is bound to the 3' end and $C_{24}$ ($C_6$—S—S—$C_{18}$) is bound to the 5' end.

After completion of the synthesis, the synthesized RNA single strand and oligo (DNA or RNA)-polymer structure were detached from the CPG by treatment with 28% (v/v) ammonia in a water bath at 60° C., and then protective residues were removed by a deprotection reaction. After removal of the protective residues, the RNA single strand and the oligo (DNA Or RNA)-polymer structure were treated with N-methylpyrrolidone, trimethylamine and triethylaminetrihydrofluoride at a volume ratio of 10:3:4 in an oven at 70° C. to remove 2'-TBDMS (tert-butyldimethylsilyl). An RNA single strand, an oligo (DNA or RNA)-polymer structure and a ligand-bound oligo (DNA or RNA)-polymer structure were separated from the reaction products by high-performance liquid chromatography (HPLC), and the molecular weights thereof were measured by a MALDI-TOF mass spectrophotometer (MALDI TOF-MS, SHIMADZU, Japan) to confirm whether they would match the nucleotide sequence and polymer structure desired to be synthesized. Thereafter, to produce each double-stranded oligo structure, the sense strand and the antisense strand were mixed together, added to 1× annealing buffer (30 mM HEPES, 100 mM potassium acetate, 2 mM magnesium acetate, pH 7.0 to 7.5), allowed to react in a water bath at 90° C. for 3 minutes, and then allowed to react at 37° C., thereby producing the desired SAMiRNA. Annealing of the produced double-stranded oligo RNA structures was confirmed by electrophoresis.

Example 3. High-Throughput Screening (HTS) of SAMiRNA Nanoparticles That Target Human Amphiregulin and Induce RNAi 3-1 Production of SAMiRNA Nanoparticles 1,257 SAMiRNAs targeting amphiregulin sequences, synthesized in Example 2, were dissolved in 1× Dulbecco's phosphate buffered saline (DPBS) (WELGENE, KR) and freeze-dried in a freeze dryer (LGJ-100F, CN) for 5 days. The freeze-dried nanoparticle powders were dissolved and homogenized in 1.429 ml of deionized distilled water (Bioneer, KR) and used in an experiment for the present invention.

3-2 Treatment of Cells with SAMiRNA Nanoparticles

To identify SAMiRNA that inhibits amphiregulin expression, the human lung cancer line A549 was used. The A549 cell line was cultured in Gibco™ Ham's F-12K (Kaighn's) medium (Thermo, US) containing 10% fetal bovine serum (Hyclone, US) and 1% penicillin-streptomycin (Hyclone, US) at 37° C. under 5% $CO_2$. Using the same medium as above, the A549 cell line was dispensed into a 96-well plate (Costar, US) at a density of 2×10$^4$ cells/well. The next day, the SAMiRNA homogenized with deionized distilled water in Example 3.1 above was diluted with 1×DPBS, and the cells were treated with the dilution to a SAMiRNA concentration of 500 nM or 1,000 nM. Treatment with the SAMiRNA was performed a total of four times (once every 12 hours), and the cells were cultured at 37° C. under 5% $CO_2$.

3-3 Screening of SAMiRNA by Inhibition Analysis of mRNA Expression of Human Amphiregulin Total RNA was extracted from the cell line treated with SAMiRNA in Example 3-2, and was synthesized into cDNA, and then the relative mRNA expression level of the amphiregulin gene was quantified by real-time PCR.

For analysis of the mRNA expression level of the amphiregulin gene, 300 nM AREG forward primer, 300 nM AREG reverse primer, 300 nM AREG probe, 300 nM RPL13A forward primer, 300 nM RPL13A reverse primer, 300 nM RPL13A probe, 400 nM TBP forward primer, 400 nM TBP reverse primer, and 300 nM TBP probe were added to each well of AccuPower® Dual-HotStart RT-qPCR kit (Bioneer, Korea) and dried (Table 2, the sequences of the primers and hydrolysis probes used in the high-throughput screening (HTS) experiment). To evaluate the performance of the prepared kit, a calibration curve was created using the A549 cell total RNA and the PCR amplification efficiency was determined (Table 3). RT-qPCR was performed under the following conditions: 95° C. for 5 min, and then 45 cycles, each consisting of 95° C. for 5 sec and 58° C. for 15 sec. A protocol in which a fluorescence value is detected in each cycle was used.

The 96-well plate (Costar, US) treated with SAMiRNA was subjected to total RNA extraction and one-step RT-qPCR according to an automated program using the automated system ExiStation HT™ Korea and the separately prepared AccuPower® Dual-HotStart RT-qPCR kit (Bioneer, Korea) comprising primers and probes for analysis of amphiregulin.

Based on the Ct values of two genes obtained after qPCR array, the relative mRNA expression level of amphiregulin in the test group compared to that in the control group was analyzed by the 2(−Delta Delta C(T)) method [Livak K J, Schmittgen T D. 2001. Analysis of relative gene expression data using real-time quantitative PCR and the 2(−Delta Delta C(T)) Method. Methods. Dec; 25(4):4 02-8].

TABLE 2

Sequences of primers and hydrolysis probes used in high-throughput screening (HTS) experiment

| | |
|---|---|
| AREG Forward primer | CAGTGCTGATGGATTTGAGGT (SEQ ID NO: 26) |
| AREG Reverse primer | ATAGCCAGGTATTTGTGGTTCG (SEQ ID NO: 27) |
| AREG probe | 5' FAM-TGAACCGTCCTCGGGAGCCGACT-3'EBQ (SEQ ID NO: 28) |
| RPL13A Forward primer | GTGTTTGACGGCATCCCACC (SEQ ID NO: 29) |
| RPL13A Reverse primer | TAGGCTTCAGACGCACGACC (SEQ ID NO: 30) |
| RPL13A probe | 5'TAMRA-AAGCGGATGGTGGTTCCTGCT-3'EBQ (SEQ ID NO: 31) |
| TBP Forward primer | CACCACAGCTCTTCCACTC (SEQ ID NO: 32) |
| TBP Reverse primer | ATCCCAGAACTCTCCGAAGC (SEQ ID NO: 33) |
| TBP probe | 5'TEXASRED-ACCCTTGCCGGGCACCACTC-3'EBQ (SEQ ID NO: 34) |

TABLE 3

| 3-plex RT-qPCR amplification efficacy | | | |
|---|---|---|---|
| | Slope | $R^2$ | Efficiency |
| AREG | Y = −0.2778X + 12.3894 | 0.9998 | 90% |
| RPL13A | Y = −0.2863X + 10.5964 | 0.9999 | 93% |
| TBP | Y = −0.2892X + 13.0351 | 0.9946 | 95% |

To select highly efficient SAMiRNA, 14 SAMiRNAs were selected, which had each of the sequences of SEQ ID NOs: 1 to 14 as a sense strand. Here, the selected SAMiRNAs showed the highest efficiency with which the mRNA expression level of amphiregulin at a final concentration of 500 nM or 1,000 nM decreased compared to the control.

As shown in FIG. 1, 14 SAMiRNAs that most effectively inhibit amphiregulin gene expression were finally selected from 1,257 SAMiRNAs targeting amphiregulin. Information on the sequences of the selected SAMiRNAs is shown in Table 4 below.

TABLE 4

Amphiregulin-specific SAMiRNA candidate sequences selected by
1-base sliding window screening and high-throughput screening (HTS)

| SEQ ID NO | Accession No. | Position | | Sequence (DNA/RNA) |
|---|---|---|---|---|
| 1 | NM_001657.3 | 8-26 | Sense | CCTATAAAGCGGCAGGTGC |
| 35 | | | Antisense | GCACCUGCCGCUUUAUAGG |
| 2 | NM_001657.3 | 130-148 | Sense | GAGCGGCGCACACTCCCGG |
| 36 | | | Antisense | CCGGGAGUGUGCGCCG CUC |
| 3 | NM_001657.3 | 195-213 | Sense | GTCCCAGAGACCGAGTTGC |
| 37 | | | Antisense | GCAACUCGGUCUCUGG GAC |
| 4 | NM_001657.3 | 224-242 | Sense | GAGACGCCGCCGCTGCGAA |
| 38 | | | Antisense | UUCGCAGCGGCGGCGU CUC |
| 5 | NM_001657.3 | 270-288 | Sense | CCGGCGCCGGTGGTGCTGT |
| 39 | | | Antisense | ACAGCACCACCGGCGC CGG |
| 6 | NM_001657.3 | 278-296 | Sense | GGTGGTGCTGTCGCTCTTG |
| 40 | | | Antisense | CAAGAGCGACAGCACC ACC |
| 7 | NM_001657.3 | 289-307 | Sense | CGCTCTTGATACTCGGCTC |
| 41 | | | Antisense | GAGCCGAGUAUCAAGA GCG |
| 8 | NM_001657.3 | 292-310 | Sense | TCTTGATACTCGGCTCAGG |
| 42 | | | Antisense | CCUGAGCCGAGUAUCA AGA |
| 9 | NM_001657.3 | 329-347 | Sense | GGACCTCAATGACACCTAC |
| 43 | | | Antisense | GUAGGUGUCAUUGAGGUCC |
| 10 | NM_001657.3 | 341-359 | Sense | CACCTACTCTGGGAAGCGT |
| 44 | | | Antisense | ACGCUUCCCAGAGUAG GUG |
| 1 | NM_001657.3 | 342-360 | Sense | ACCTACTCTGGGAAGCGTG |
| 45 | | | Antisense | CACGCUUCCCAGAGUA GGU |
| 12 | NM_001657.3 | 349-367 | Sense | CTGGGAAGCGTGAACCATT |
| 46 | | | Antisense | AAUGGUUCACGCUUCC CAG |
| 13 | NM_001657.3 | 353-371 | Sense | GAAGCGTGAACCATTTTCT |
| 47 | | | Antisense | AGAAAAUGGUUCACGC UUC |
| 14 | NM_001657.3 | 368-386 | Sense | TTCTGGGGACCACAGTGCT |
| 48 | | | Antisense | AGCACUGUGGUCCCCA GAA |

Example 4. Screening of SAMiRNA Nanoparticles that Target Human Amphiregulin and Induce RNAi The lung cancer cell line A549 was treated with SAMiRNA (selected in Example 3) having each of the sequences of SEQ ID NOs: 1 to 14 as a sense strand, and the expression pattern of amphiregulin mRNA in the cell line was analyzed.

4-1 Treatment of Cells with SAMiRNA Nanoparticles

To identify SAMiRNA that inhibits amphiregulin expression, the human lung cancer line A549 was used. The A549 cell line was cultured in Gibco™ Ham's F-12K (Kaighn's) medium (Thermo, US) containing 10% fetal bovine serum (Hyclone, US) and 1% penicillin-streptomycin (Hyclone, US) at 37° C. under 5% $CO_2$. Using the same medium as above, the A549 cell line was dispensed into a 12-well plate (Costar, US) at a density of $8\times10^4$ cells/well. The next day, the SAMiRNA homogenized with deionized distilled water in Example 3.1 above was diluted with 1×DPBS, and the cells were treated with the dilution to a SAMiRNA concentration of 200 nM or 600 nM. Treatment with the SAMiRNA was performed a total of four times (once every 12 hours), and the cells were cultured at 37° C. under 5% $CO_2$.

4-2 Screening of SAMiRNA by Inhibition Analysis of Human Amphiregulin mRNA Expression Total RNA was extracted from the cell line treated with SAMiRNA in Example 4-1 and was synthesized into cDNA, and then the relative mRNA expression level of the amphiregulin gene was quantified by real-time PCR.

4-2-1 RNA Isolation from SAMiRNA-Treated Cells and cDNA Synthesis

Using an RNA extraction kit (AccuPrep Cell total RNA extraction kit, BIONEER, Korea), total RNA was extracted from the cell line treated with SAMiRNA in Example 4-1 above. The extracted RNA was synthesized into cDNA in the following manner using RNA reverse transcriptase (AccuPower® RocketScript™ Cycle RT Premix with oligo (dT) 20, Bioneer, Korea). Specifically, 1 µg of the extracted RNA was added to AccuPower® RocketScript™ Cycle RT Premix with oligo (dT)20 (Bioneer, Korea) in each 0.25 ml Eppendorf tube, and distilled water treated with DEPC (diethyl pyrocarbonate) was added thereto to a total volume of 20 µl. In a gene amplification system (MyGenie™ 96 Gradient Thermal Block, BIONEER, Korea), a process of hybridizing the RNA with primers at 37° C. for 30 seconds and a process of synthesizing cDNA at 48° C. for 4 minutes were repeated 12 times. Then, the amplification reaction was terminated by deactivating the enzyme at 95° C. for 5 minutes.

4-2-2 Quantitative Analysis of Relative mRNA Expression Level of Human Amphiregulin mRNA Using the cDNA synthesized in Example 4-2-1 as a template, SYBR green real-time qPCR was performed, and the relative mRNA expression level of amphiregulin compared to a SAMiRNA control sample was analyzed in the following manner. The cDNA synthesized in Example 4-2-1 above was diluted 5-fold with distilled water, and for analysis of the mRNA expression level of amphiregulin, 3 μl of the diluted cDNA, 25 μl of AccuPower® 2× GreenStar™ qPCR MasterMix (BIONEER, Korea), 19 μl of distilled water, and 3 μl of amphiregulin qPCR primers (SEQ ID NOs: 17 and 18 (Table 5); 10 pmole/μl for each primer, BIONEER, Korea) were added to each well of a 96-well plate to make a mixture. Meanwhile, GAPDH (glyceraldehyde 3-phosphate dehydrogenase), a housekeeping gene (hereinafter referred to as HK gene), was used as a standard gene to normalize the mRNA expression level of amphiregulin. The 96-well plate containing the mixture was subjected to the following reaction using Exicycler™ Real-Time Quantitative Thermal Block (BIONEER, Korea). Specifically, the mixture was allowed to react at 95° C. for 15 minutes to activate the enzyme and remove the secondary structure of the cDNA, and then the mixture was subjected to 42 cycles, each consisting of denaturation at 94° C. for 30 sec, annealing at 58° C. for 30 sec, extension at 72° C. for 30 sec, and SYBR green scan, and to final extension at 72° C. for 3 minutes. Next, the mixture was maintained at a temperature of 55° C. for 1 minute, and the melting curve from 55° C. to 95° C. was analyzed.

After completion of the PCR, the Ct (threshold cycle) value of the target gene was corrected by the GAPDH gene, and then the ΔCt value was calculated using a control treated with the control sequence SAMiRNA (SAMiCONT) that does not induce gene expression inhibition. The relative expression level of the target gene in the cells treated with the amphiregulin-specific SAMiRNA was quantified using the ΔCt value and the equation 2(−ΔCt)×100.

To select highly efficient SAMiRNAs, 14 SAMiRNAs were selected, which had each of the sequences of SEQ ID NOs: 10, 11 and 12 as a sense strand. Here, the selected SAMiRNAs showed the highest efficiency with which the mRNA expression level of amphiregulin at a final concentration of 200 nM or 600 nM decreased compared to the control.

Figure 3A:
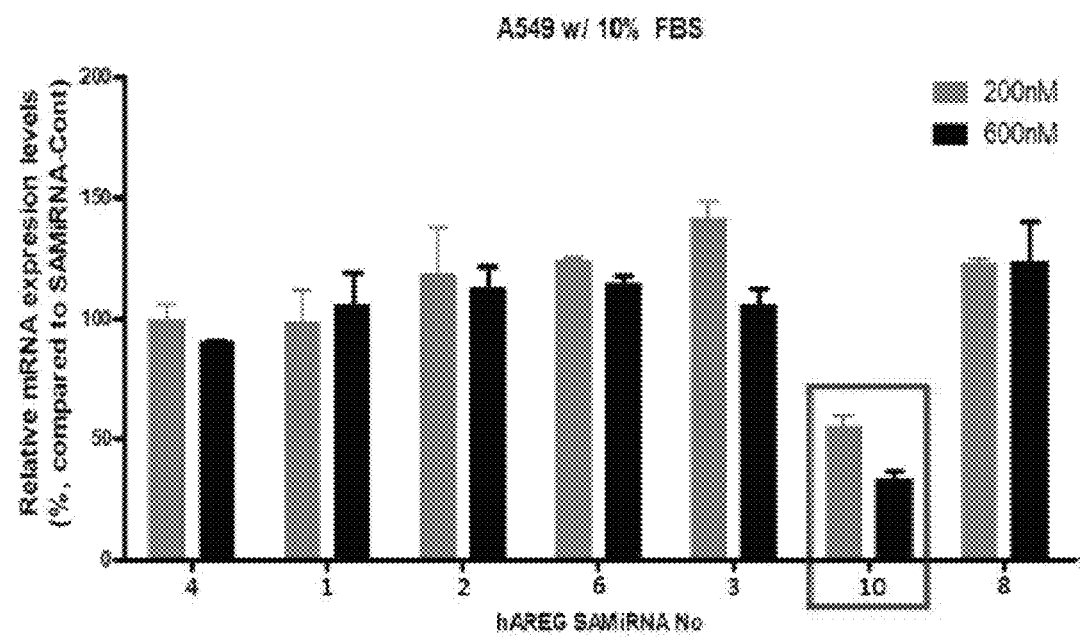
FIGS. 3a and 3B show the results of quantitatively analyzing the mRNA expression levels of amphiregulin in Example 4, and depicts graphs showing the relative mRNA expression levels (%) of amphiregulin in the lung cancer cell line A549 with different concentrations (200 and 600 nM) of SAMiRNA having each of the sequences of SEQ ID NOs: 1 to 14 of the present invention as a sense strand.
Figure 3B:
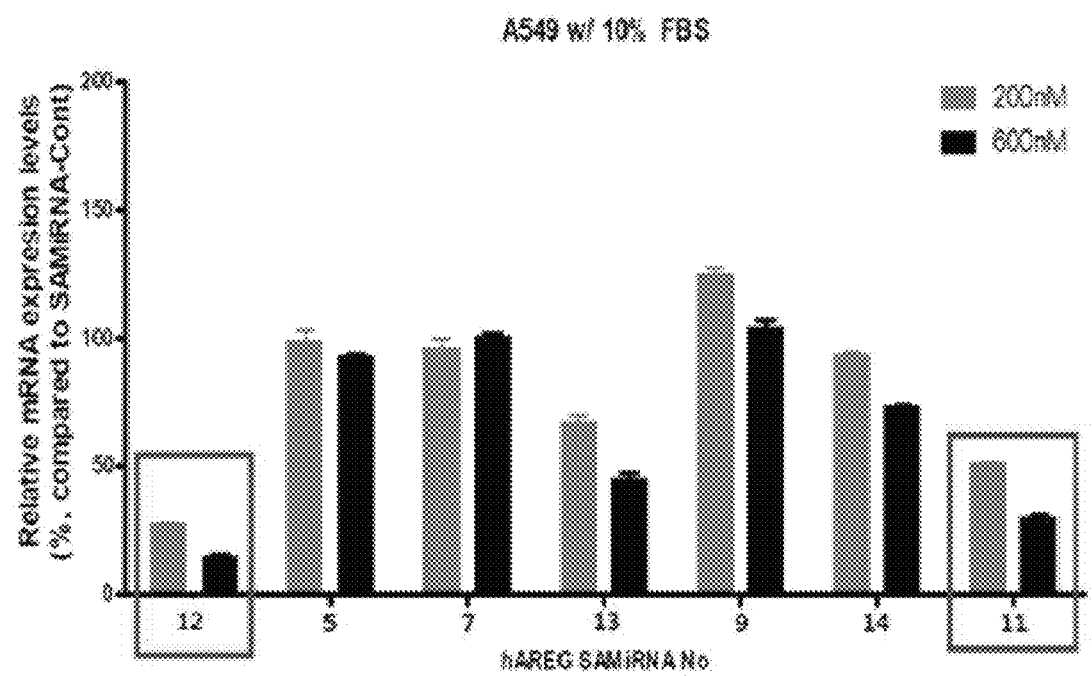

As shown in FIG. 3, three SAMiRNAs that most effectively inhibit amphiregulin gene expression were finally selected from 14 SAMiRNAs targeting amphiregulin. Information on the sequences of the selected SAMiRNAs is shown in Table 6 below.

TABLE 5

Information on primer sequences for qPCR

| Primer | Sequence | SEQ ID NO |
|---|---|---|
| hGAPDH-F | GGTGAAGGTCGGAGTCAACG | 15 |
| hGAPDH-R | ACCATGTAGTTGAGGTCAATGAAGG | 16 |
| hAREG-F | ACACCTACTCTGGGAAGCGT | 17 |
| hAREG-R | GCCAGGTATTTGTGGTTCGT | 18 |

(F denotes a forward primer, and R denotes a reverse primer)

TABLE 6

SAMiRNA sequences that effectively inhibit amphiregulin expression

| SEQ ID NO | Code Name | Position | Sense strand sequence |
|---|---|---|---|
| 10 | SAMi-AREG#10 | 341-359 | CACCTACTCTGGGAAGCGT |
| 11 | SAMi-AREG#11 | 342-360 | ACCTACTCTGGGAAGCGTG |
| 12 | SAMi-AREG#12 | 349-367 | CTGGGAAGCGTGAACCATT |

Example 5. Inhibition of Human Amphiregulin Expression in Lung Cancer Cell Line (A549) by Selected SAMiRNAs The lung cancer cell line A549 was treated with the SAMiRNA (selected in Example 4) having each of the sequences of SEQ ID NOs: 10, 11 and 12 as a sense strand, and the expression pattern of amphiregulin mRNA in the cell line was analyzed to determine the $IC_{50}$ value of the SAMiRNA.

5-1 Production and Particle Size Analysis of SAMiRNA Nanoparticles

Figure 2A:
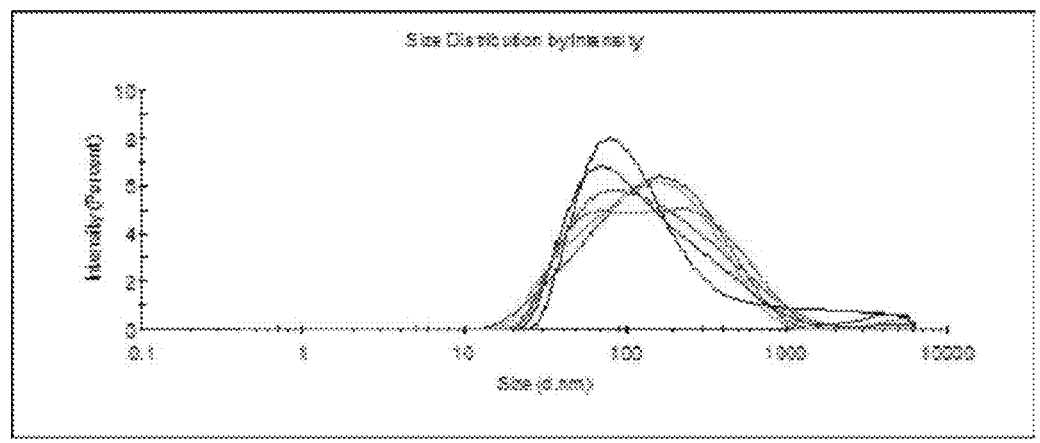
FIGS. 2A, 2B, and 2C show the nanoparticle size distributions of double-stranded DNA/RNA hybrids comprising selected amphiregulin-specific double-stranded oligonucleotides.
Figure 2B:
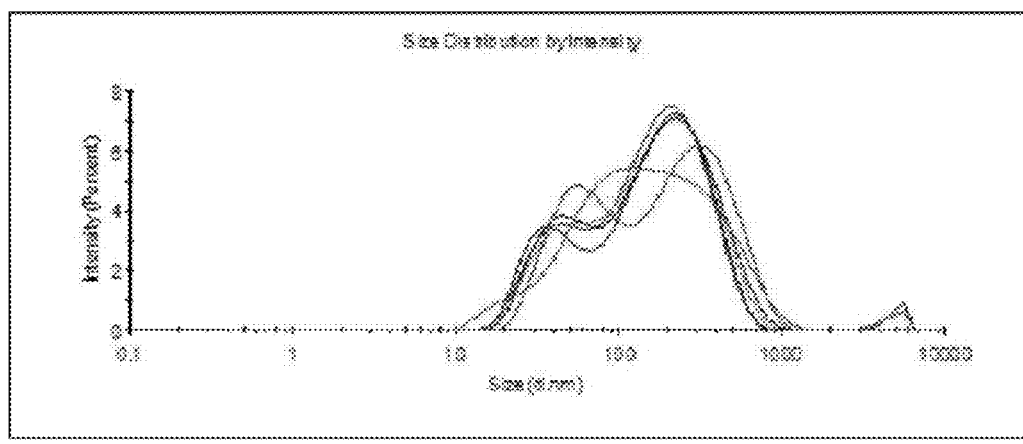
Figure 2C:
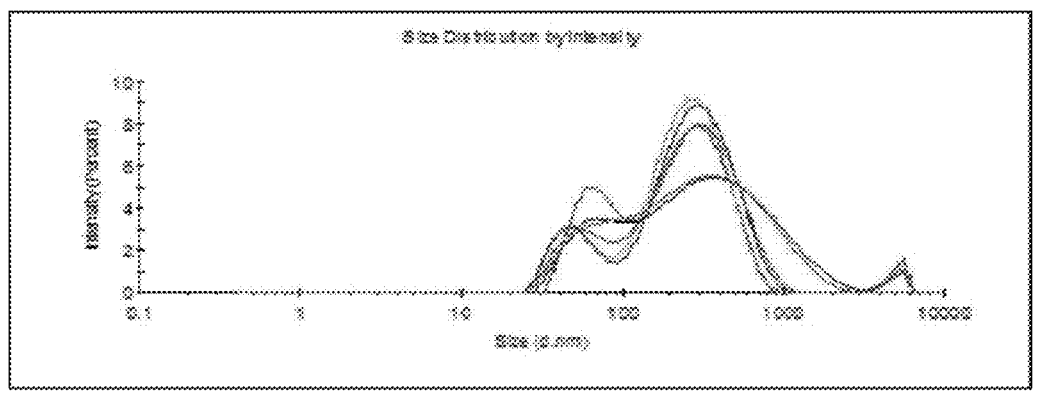

Each of the three SAMiRNAs targeting the amphiregulin sequence, synthesized in Example 2, was dissolved in 1× Dulbecco's phosphate buffered saline (DPBS) (WELGENE, KR) and freeze-dried in a freeze dryer (LGJ-100F, CN) for 5 days. The freeze-dried nanoparticle powders were dissolved and homogenized in 2 ml of deionized distilled water (Bioneer, KR) and used in an experiment for the present invention. To analyze the particle size of the produced SAMiRNA nanoparticles, the size and polydispersity index of the SAMiRNA were measured using Zetasizer Nano ZS (Malvern, UK). The results of measuring the size and polydispersity index of the SAMiRNA nanoparticles are shown in Table 7 below and graphically shown in FIG. 2.

TABLE 7

Size and polydispersity index of amphiregulin-specific SAMiRNA nanoparticles

| Code Name | Size | PDI |
|---|---|---|
| SAMi-AREG#10 | 103.9 ± 3.8 | 0.406 ± 0.065 |
| SAMi-AREG#11 | 99.9 ± 4.0 | 0.501 ± 0.005 |
| SAMi-AREG#12 | 170.1 ± 7.5 | 0.457 ± 0.084 |

5-2 Treatment of Cells with SAMiRNA Nanoparticles

To evaluate the effect of the selected SAMiRNAs that inhibit amphiregulin expression, the human lung cancer cell line A549 was used. The A549 cell line was cultured in Gibco™ Ham's F-12K (Kaighn's) medium (Thermo, US) containing 10% fetal bovine serum (Hyclone, US) and 1% penicillin-streptomycin (Hyclone, US) at 37° C. under 5% $CO_2$. Using the same medium as above, the A549 cell line was dispensed into a 12-well plate (Costar, US) at a density of (Costar, US) $8 \times 10^4$ cells/well. The next day, the SAMiRNA homogenized with deionized distilled water in Example 5.1 above was diluted with 1×DPBS, and the cells were treated with the dilution to a SAMiRNA concentration of 12.5 nM, 25 nM, 50 nM, 100 nM, 200 nM, 600 nM or 1200 nM. Treatment of the cells with the SAMiRNA was performed a total of four times (once every 12 hours), and the cells were cultured at 37° C. under 5% $CO_2$.

5-3 Determination of $IC_{50}$ of SAMiRNA by Inhibition Analysis of mRNA Expression of Human Amphiregulin Total RNA was extracted from the cell line treated with the SAMiRNA in Example 5-2 and was synthesized into cDNA, and then the relative mRNA expression level of the amphiregulin gene was quantified by real-time PCR.

5-3-1 RNA Isolation from SAMiRNA-Treated Cells and cDNA Synthesis

Using an RNA extraction kit (AccuPrep Cell total RNA extraction kit, BIONEER, Korea), total RNA was extracted from the cell line treated with the SAMiRNA in Example 5-2 above. The extracted RNA was synthesized into cDNA in the following manner using RNA reverse transcriptase (AccuPower® RocketScript™ Cycle RT Premix with oligo (dT)20, Bioneer, Korea). Specifically, 1 µg of the extracted RNA was added to AccuPower® RocketScript™ Cycle RT Premix with oligo (dT)20 (Bioneer, Korea) in each 0.25 ml Eppendorf tube, and distilled water treated with DEPC (diethyl pyrocarbonate) was added thereto to a total volume of 20 µl. In a gene amplification system (MyGenie™96 Gradient Thermal Block, BIONEER, Korea), a process of hybridizing the RNA with primers at 37° C. for 30 seconds and a process of synthesizing cDNA at 48° C. for 4 minutes were repeated 12 times. Then, the amplification reaction was terminated by deactivating the enzyme at 95° C. for 5 minutes.

5-3-2 Quantitative Analysis of Relative mRNA Expression Level of Human Amphiregulin Using the cDNA synthesized in Example 5-3-1 as a template, SYBR green real-time qPCR was performed, and the relative mRNA expression level of amphiregulin compared to a SAMiRNA control sample was analyzed in the following manner. The cDNA synthesized in Example 5-3-1 above was diluted 5-fold with distilled water, and for analysis of the mRNA expression level of amphiregulin, 3 µl of the diluted cDNA, 25 µl of AccuPower® 2× GreenStar™ qPCR MasterMix (BIONEER, Korea), 19 µl of distilled water, and 3 µl of amphiregulin qPCR primers (SEQ ID NOs: 17 and 18 (Table 5); 10 pmole/µl for each primer, BIONEER, Korea) were added to each well of a 96-well plate to make a mixture. Meanwhile, GAPDH (glyceraldehyde 3-phosphate dehydrogenase), a housekeeping gene (hereinafter referred to as HK gene), was used as a standard gene to normalize the mRNA expression level of amphiregulin. The 96-well plate containing the mixture was subjected to the following reaction using Exicycler™ Real-Time Quantitative Thermal Block (BIONEER, Korea). Specifically, the mixture was allowed to react at 95° C. for 15 minutes to activate the enzyme and remove the secondary structure of the cDNA, and then the mixture was subjected to 42 cycles, each consisting of denaturation at 94° C. for 30 sec, annealing at 58° C. for 30 sec, extension at 72° C. for 30 sec, and SYBR green scan, and to final extension at 72° C. for 3 minutes. Next, the mixture was maintained at a temperature of 55° C. for 1 minute, and the melting curve from 55° C. to 95° C. was analyzed.

After completion of the PCR, the Ct (threshold cycle) value of the target gene was corrected by the GAPDH gene was determined, and then the ΔCt value was calculated using a control treated with the control sequence SAMiRNA (SAMiCONT) that does not induce gene expression inhibition. The relative expression level of the target gene in the cells treated with the amphiregulin-specific SAMiRNA was quantified using the ΔCt value and the equation 2(−ΔCt)× 100.

Figure 4A:
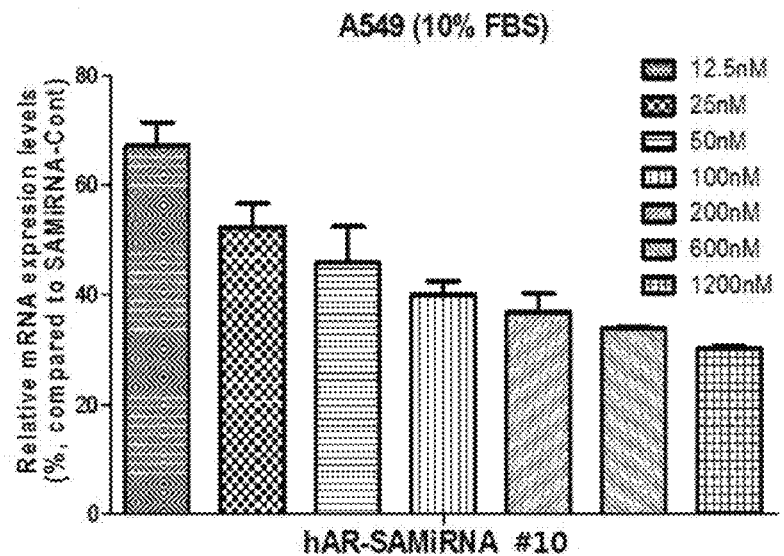
FIGS. 4A and 4B show the results of quantitatively analyzing the expression level of amphiregulin mRNA in Example 5, and depicts graphs showing the results of analyzing the relative mRNA expression levels (%) of amphiregulin (FIG. 4A) and determining the $IC_{50}$ value of SAMiRNA (FIG. 4B) in the lung cancer cell line A549 treated with different concentrations (12.5 nM, 25 nM, 50 nM, 100 nM, 200 nM, 600 nM and 1,200 nM) of SAMiRNA having the sequence of SEQ ID NO: 10 of the present invention as a sense strand.
Figure 4B:
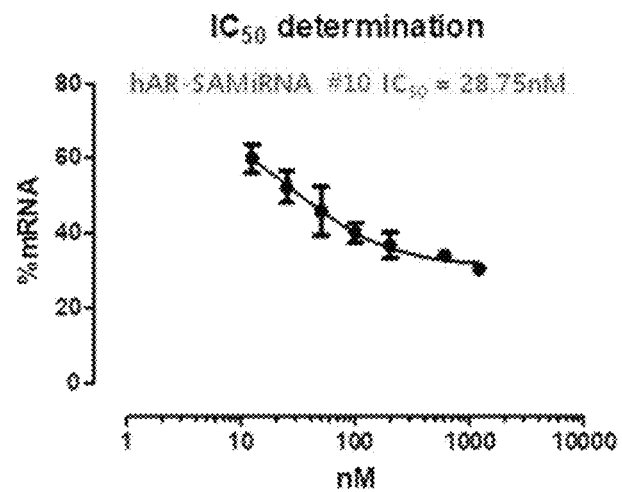
Figure 5A:
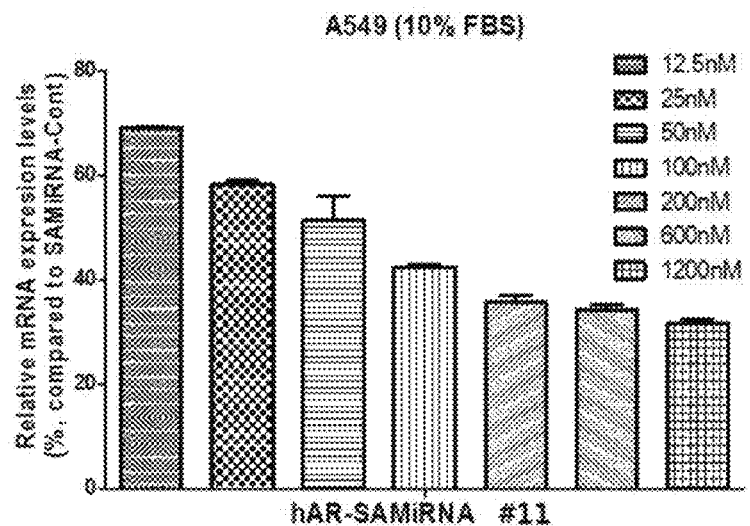
FIGS. 5A and 5B show the results of quantitatively analyzing the expression level of amphiregulin mRNA in Example 5, and depicts graphs showing the results of analyzing the relative expression levels (%) of amphiregulin mRNA (FIG. 5A) and determining the $IC_{50}$ value of SAMiRNA (FIG. 5B) in the lung cancer cell line A549 treated with different concentrations (12.5 nM, 25 nM, 50 nM, 100 nM, 200 nM, 600 nM and 1,200 nM) of SAMiRNA having the sequence of SEQ ID NO: 11 of the present invention as a sense strand.
Figure 5B:
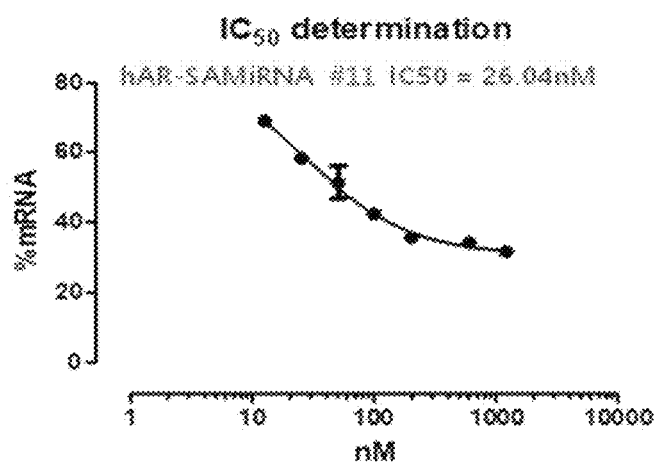
Figure 6A:
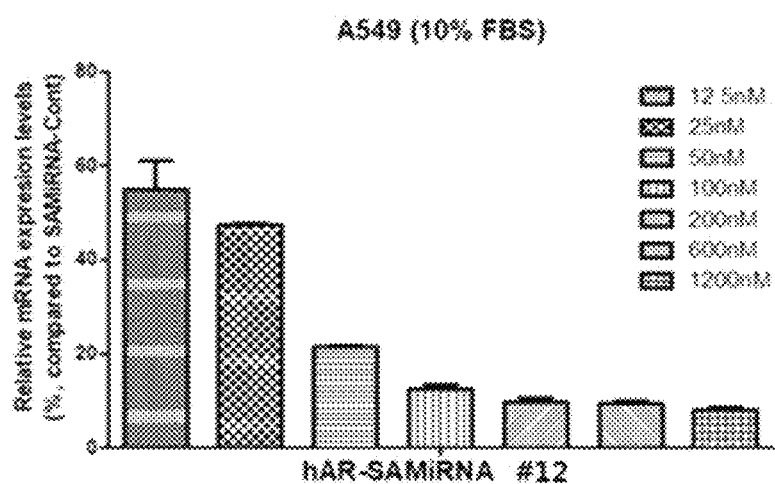
FIGS. 6A and 6B show the results of quantitatively analyzing the expression level of amphiregulin mRNA in Example 5, and depicts graphs showing the results of analyzing the relative expression levels (%) of amphiregulin mRNA (FIG. 6A) and determining the $IC_{50}$ value of SAMiRNA (FIG. 6B) in the lung cancer cell line A549 treated with different concentrations (12.5 nM, 25 nM, 50 nM, 100 nM, 200 nM, 600 nM and 1,200 nM) of SAMiRNA having the sequence of SEQ ID NO: 12 of the present invention as a sense strand.
Figure 6B:
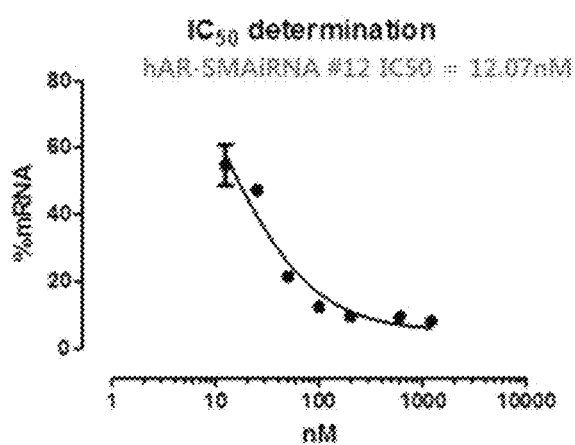

As a result, it was confirmed that all the amphiregulin-specific SAMiRNAs having each of the sequences of SEQ ID NOs: 10, 11 and 12 as a sense strand showed a 50% or more decrease in the mRNA expression level of amphiregulin even at a low concentration of 100 nM, suggesting that the amphiregulin-specific SAMiRNAs exhibited the effect of inhibiting amphiregulin expression with high efficiency. It was confirmed that the $IC_{50}$ values were 28.75 nM as shown in FIG. 4 for the amphiregulin-specific SAMiRNA having the sequence of SEQ ID NO: 10 as a sense strand, 26.04 nM as shown in FIG. 5 for the amphiregulin-specific SAMiRNA having the sequence of SEQ ID NO: 11 as a sense strand, and 12.07 nM as shown in FIG. 6 for the amphiregulin-specific SAMiRNA having the sequence of SEQ ID NO: 12 as a sense strand. In particular, it was confirmed that the amphiregulin-specific SAMiRNA having the sequence of SEQ ID NO: 12 as a sense strand showed a 50% or more decrease in the mRNA expression level of amphiregulin even at a low concentration of 25 nM as shown in FIG. 6, suggesting that it exhibited the effect of most effectively inhibiting amphiregulin gene expression among the three selected sequences.

Example 6. Evaluation of In Vitro Cytotoxicity Using Human Peripheral Blood Mononuclear Cells (PBMCs)

In order to examine whether the mRNA expression levels of innate immune-related cytokines are increased by SAMi-hAREG, ePBMC® cryopreserved human PBMCs (human peripheral monocular cells), Cellular Technology Limited, USA) were dispensed at a density of $5 \times 10^5$ cells per well into a 12-well plate (Costar® USA) with RPMI1640 (Hyclone™) medium containing 10% FBS (fetal bovine serum; Hyclone™) The cells were cultured in a 5% $CO_2$ incubator at 37° C. for 1 hour so as to be stabilized, and then the dispensed PBMCs were treated with 2.5 µM of each of SAMi-CON (DNA/RNA), SAMi-hAREG #10 (DNA/RNA), SAMi-hAREG #11 (DNA/RNA), SAMi-hAREG #12 (DNA/RNA), SAMi-CON (RNA/RNA), SAMi-hAREG #10 (RNA/RNA), SAMi-hAREG #11 (RNA/RNA), an d SAMi-hAREG #12 (RNA/RNA), and cultured in a 5% $CO_2$ incubator at 37° C. for 6 hours. As a positive control, 20 µg/ml of Concanavalin A (Sigma Aldrich, USA) was used.

Thereafter, all the cells were harvested, and total RNA was extracted therefrom using an RNeasy Mini Kit (Qiagen, Germany) and an RNase-Free DNase Set (Qiagen, Germany) according to the manufacturer's protocols.

200 ng of the extracted RNA was mixed with deionized sterile DW (Bioneer, Korea) and RNA reverse transcriptase (AccuPower® RocketScript™ Cycle RT Premix with oligo (dT)20, Bioneer, Korea), and the mixture was allowed to react using a gene amplification system (MyGenie™96 Gradient Thermal Block, BIONEER, Korea) under conditions of 12 cycles, each consisting of 37° C. for 30 sec, 48° C. for 4 min and 55° C. for 30 sec, and then 95° C. for 5 min, thereby synthesizing a total of 20 µl of cDNA.

The synthesized cDNA was mixed with qPCR primers for each of RPL13A, IL1B, IL6, IFNG, TNF and IL12B genes and then amplified using Exicycler™96 Real-Time Quantitative Thermal Block (Bioneer, Korea) under the following conditions: 95° C. for 5 min, and then 45 cycles, each consisting of 95° C. for 5 sec and 58° C. for 15 sec.

Based on the Ct values of two genes obtained after qPCR array, the relative mRNA expression level in the test group compared to that in the control group was analyzed by the 2(−Delta Delta C(T)) Method [Livak K J, Schmittgen T D.

2001. Analysis of relative gene expression data using real-time quantitative PCR and the 2(−Delta Delta C(T)) Method. Methods. Dec; 25(4):4 02-8].

Figure 7A:
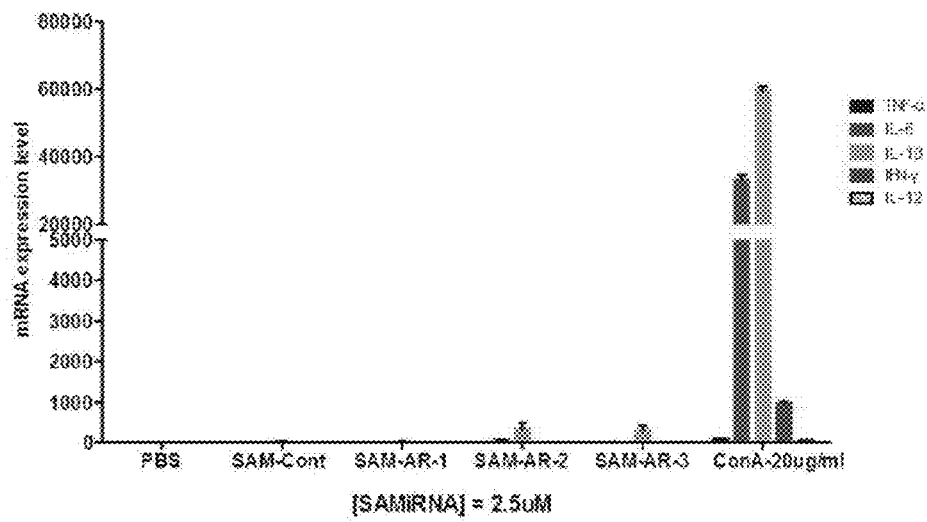
FIGS. 7A and 7B show the results of an innate immune response test for amphiregulin candidate sequences in Example 6, and depicts the results obtained by treating human peripheral blood mononuclear cells (PBMCs) with 2.5 µM of amphiregulin-specific SAMiRNA having each of the sequences of SEQ ID NOs: 10 (AR-1), 11 (AR-2) and 12 (AR-3) of the present invention as a sense strand, analyzing the relative increases in mRNA expression levels of innate immune-related cytokines by amphiregulin-specific SAMiRNA, and evaluating in vitro cytotoxicity using the human peripheral blood mononuclear cells.
Figure 7B:
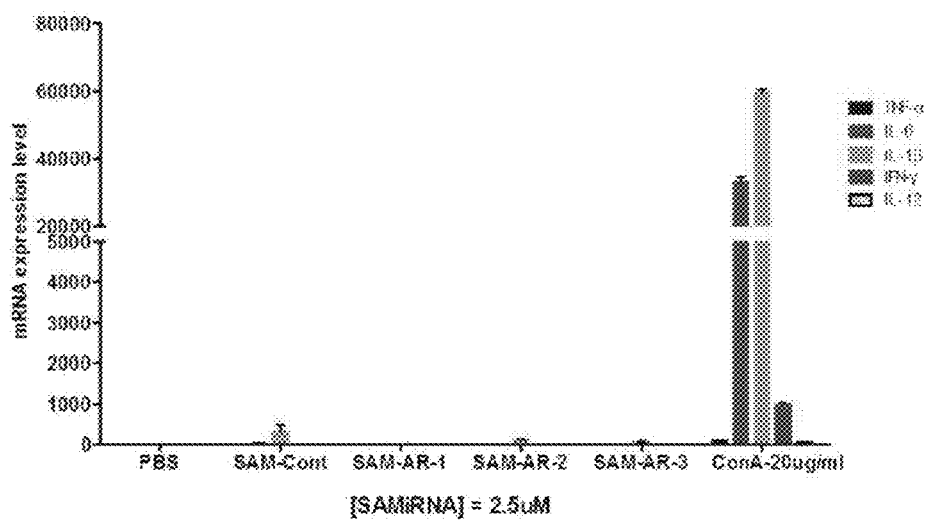

As a result, as shown in FIG. 7, it was confirmed that the expression of innate immune-related cytokines in the human peripheral blood mononuclear cells (human PBMCs) by each of amphiregulin-specific SAMiRNA #10, SAMiRNA #11 and SAMiRNA #12 was not observed.

Example 7. Comparative Analysis of Human Amphiregulin Expression Inhibition by DNA/RNA Hybrid and RNA/RNA Hybrid SAMiRNAs Comprising Each of Selected Sequences of SEQ ID NOs: 10, 11 and 12 as Sense Strand The lung cancer cell line A549 was treated with each of a double stranded DNA/RNA hybrid and RNA/RNA hybrid comprising the amphiregulin-specific SAMiRNA (selected in Example 4) having each of the sequences of SEQ ID NOs: 10, 11 and 12 as a sense strand, and the relative mRNA expression levels (%) of amphiregulin in the cell line were comparatively analyzed.

7-1 Treatment of Cells with SAMiRNA Nanoparticles

To identify SAMiRNA that inhibits amphiregulin expression, the human lung cancer line A549 was used. The A549 cell line was cultured in Gibco™ Ham's F-12K (Kaighn's) medium (Thermo, US) containing 10% fetal bovine serum (Hyclone, US) and 1% penicillin-streptomycin (Hyclone, US) at 37° C. under 5% $CO_2$. Using the same medium as above, the A549 cell line was dispensed into a 12-well plate (Costar, US) at a density of $8\times10^4$ cells/well. The next day, the SAMiRNA homogenized with deionized distilled water in Example 3.1 above was diluted with 1×DPBS, and the cells were treated with the dilution to a SAMiRNA concentration of 200 nM, 600 nM or 1200 nM. Treatment of the cells with the SAMiRNA was performed a total of four times (once every 12 hours), and the cells were cultured at 37° C. under 5% $CO_2$.

7-2 Screening of SAMiRNA by Inhibition Analysis of mRNA Expression of Human Amphiregulin Total RNA was extracted from the cell line treated with SAMiRNA in Example 7-1 and was synthesized into cDNA, and then the relative mRNA expression level of the amphiregulin gene was quantified by real-time PCR.

7-2-1 RNA Isolation from SAMiRNA-Treated Cells and cDNA Synthesis

Using an RNA extraction kit (AccuPrep Cell total RNA extraction kit, BIONEER, Korea), total RNA was extracted from the cell line treated with SAMiRNA in Example 7-1 above. The extracted RNA was synthesized into cDNA in the following manner using RNA reverse transcriptase (AccuPower® RocketScript™ Cycle RT Premix with oligo (dT)20, Bioneer, Korea). Specifically, 1 μg of the extracted RNA was added to AccuPower® RocketScript™ Cycle RT Premix with oligo (dT)20 (Bioneer, Korea) in each 0.25 ml Eppendorf tube, and distilled water treated with DEPC (diethyl pyrocarbonate) was added thereto to a total volume of 20 μl. In a gene amplification system (MyGenie™96 Gradient Thermal Block, BIONEER, Korea), a process of hybridizing the RNA with primers at 37° C. for 30 seconds and a process of synthesizing cDNA at 48° C. for 4 minutes were repeated 12 times. Then, the amplification reaction was terminated by deactivating the enzyme at 95° C. for 5 minutes.

7-2-2 Quantitative Analysis of Relative mRNA Expression Level of Human Amphiregulin Using the cDNA synthesized in Example 7-2-1 as a template, SYBR green real-time qPCR was performed, and the relative mRNA expression level of amphiregulin compared to a SAMiRNA control sample was analyzed in the following manner. The cDNA synthesized in Example 7-2-1 above was diluted 5-fold with distilled water, and for analysis of the mRNA expression level of amphiregulin, and 3 μl of the diluted cDNA, 25 μl of AccuPower® 2× GreenStar™ qPCR MasterMix (BIONEER, Korea), 19 μl of distilled water, and 3 μl of amphiregulin qPCR primers (SEQ ID NOs: 17 and 18 (Table 5); 10 pmole/μl for each primer, BIONEER, Korea) were added to each well of a 96-well plate to make a mixture. Meanwhile, GAPDH (glyceraldehyde 3-phosphate dehydrogenase), a housekeeping gene (hereinafter referred to as HK gene), was used as a standard gene to normalize the mRNA expression level of amphiregulin. The 96-well plate containing the mixture was subjected to the following reaction using Exicycler™ Real-Time Quantitative Thermal Block (BIONEER, Korea). Specifically, the mixture was allowed to react at 95° C. for 15 minutes to activate the enzyme and remove the secondary structure of the cDNA, and then the mixture was subjected to 42 cycles, each consisting of denaturation at 94° C. for 30 sec, annealing at 58° C. for 30 sec, extension at 72° C. for 30 sec, and SYBR green scan, and to final extension at 72° C. for 3 minutes. Next, the mixture was maintained at a temperature of 55° C. for 1 minute, and the melting curve from 55° C. to 95° C. was analyzed.

After completion of the PCR, the Ct (threshold cycle) value of the target gene was corrected by the GAPDH gene, and then the ΔCt value was calculated using a control treated with the control sequence SAMiRNA (SAMiCONT) that does not induce gene expression inhibition. The relative expression level of the target gene was quantified using the ΔCt value and the equation 2(−ΔCt)×100.

To select highly efficient SAMiRNA from the double-stranded DNA/RNA hybrid and RNA/RNA hybrid, the DNA/RNA hybrid SAMiRNA having the sequence of SEQ ID NO: 12 as a sense strand was finally selected. Here, the selected sequence DNA/RNA hybrid SAMiRNA (a gene expression inhibition of 90% or more) showed the highest efficiency with the mRNA expression level of amphiregulin at a final concentration of 200 nM, 600 nM or 1200 nM decreased compared to the control.

Figure 8:
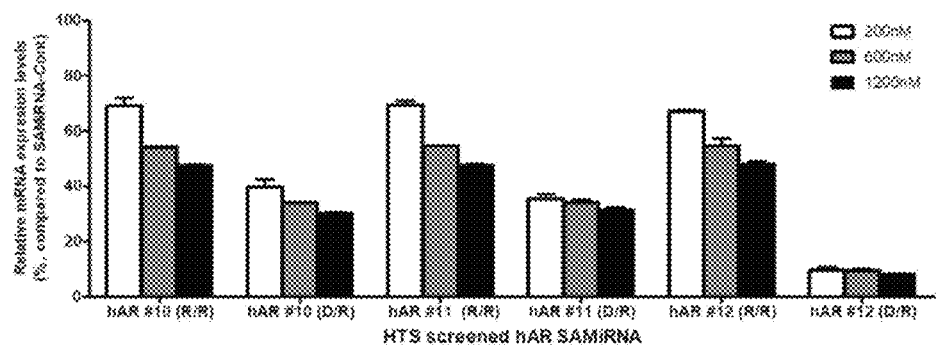
FIG. 8 shows the results of quantitatively analyzing the mRNA expression levels of amphiregulin in Example 7, and is a graph comparing the relative mRNA expression levels (%) of amphiregulin by a double-stranded oligo DNA/RNA hybrid and an RNA/RNA hybrid, each comprising selected amphiregulin-specific SAMiRNA. That is.

As shown in FIG. 8, the DNA/RNA hybrid SAMiRNA 12 that most effectively inhibits amphiregulin gene expression was finally selected from the DNA/RNA and RNA/RNA hybrids comprising the three selected amphiregulin-specific SAMiRNAs, respectively.

Example 8. High-Throughput Screening (HTS) of SAMiRNA Nanoparticles that Target Mouse Amphiregulin and Induce RNAi In the case of siRNA therapeutic agents, it is difficult to identify an optimal sequence that is applicable to different strains. In this case, US FDA guidelines are applied, according to which a DNA sequence (surrogate sequence; mouse gene-specific siRNA) specific for an animal model for analysis of therapeutic effects (an in vivo efficacy test) is designed so as to verify pharmacological activity resulting from the inhibition of expression of the gene of interest and toxicity resulting from the inhibition of expression of the gene of interest (presentation by Robert T. Dorsam Ph.D. Pharmacology/Toxicology Reviewer, FDA/CDER).

Figure 9A:
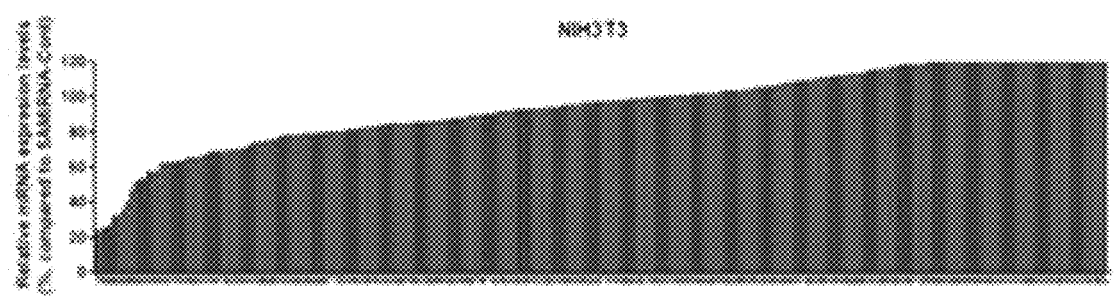
FIGS. 9A and 9B show the results of screening 237 SAMiRNA, which target mouse amphiregulin, and 9 candidate sequences selected therefrom.
Figure 9B:
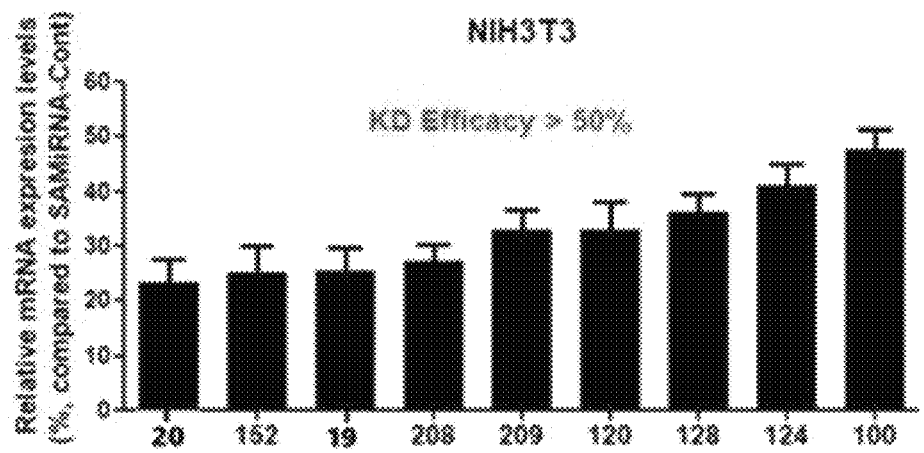

Previously discovered screening was modified by existing algorithm-based siRNA program (Turbo-si-designer owned by the applicant's company), and SAMiRNA-based siRNA sequence high-throughput screening was performed. 1-base sliding window scanning (the same method as the above-described human amphiregulin target screening) of 19-mer siRNAs against the entire target gene was performed, and a total of 1,190 candidate siRNA sequences against the possible mouse amphiregulin gene (NM_009704.4) full transcript sequence were generated. Blast sequence homology filtering was performed to remove unnecessary candidate sequences that influence the expression of other genes, and 237 finally selected SAMiRNAs were synthesized. The mouse NIH3T3 cell line was treated with each selected SAMiRNA at a concentration of 1 μM in a cell culture medium containing 10% FBS, and the in vitro expression inhibitory effects of the SAMiRNAs were first screened using the primers shown in Table 8 (primer sequence information for qPCR) (FIG. 9).

Figure 10A:
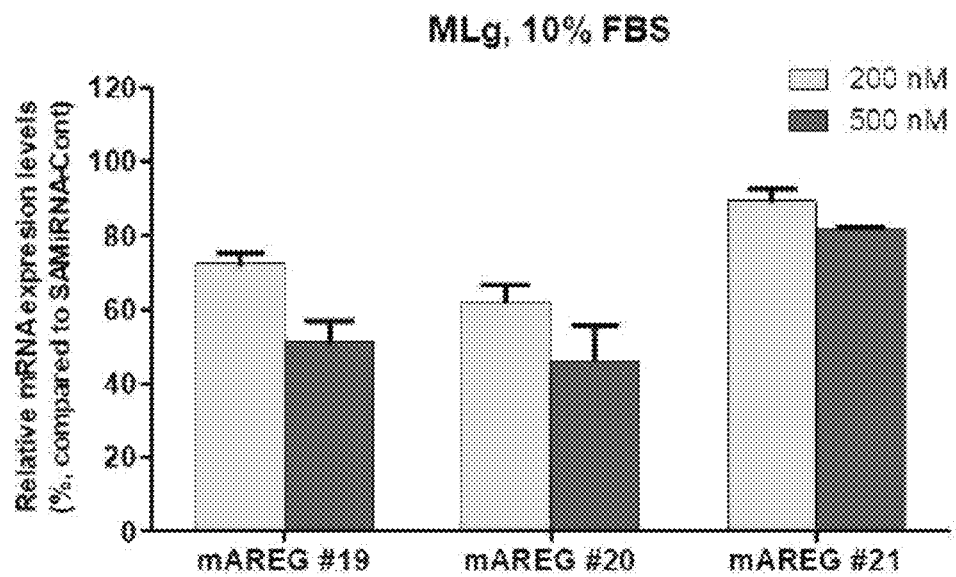
FIG. 10A shows the results of quantitatively analyzing the mRNA expression levels of mouse amphiregulin in Example 8, and is a graph showing the relative mRNA expression levels (%) of amphiregulin in the mouse lung fibroblast cell line MLg treated with different concentrations (200 and 500 nM) of SAMiRNA having each of the sequences of SEQ ID NOs: 19, 20 and 21 of the present invention as a sense strand.

Thereafter, the mouse lung fibroblast cell line MLg was treated with each of the two sequences (SEQ ID NOs: 19 and 20) selected in the NIH3T3 cell line and the mouse SAMiRNA-amphiregulin of SEQ ID NO: 21 discovered through previous milestone studies, at treatment concentrations of 200 nM and 500 nM in cell culture media containing 10% FBS, and additional screening was performed. As a result, it was confirmed that SEQ ID NO: 20 exhibited the best expression inhibitory effect (FIG. 10A).

Figure 10B:
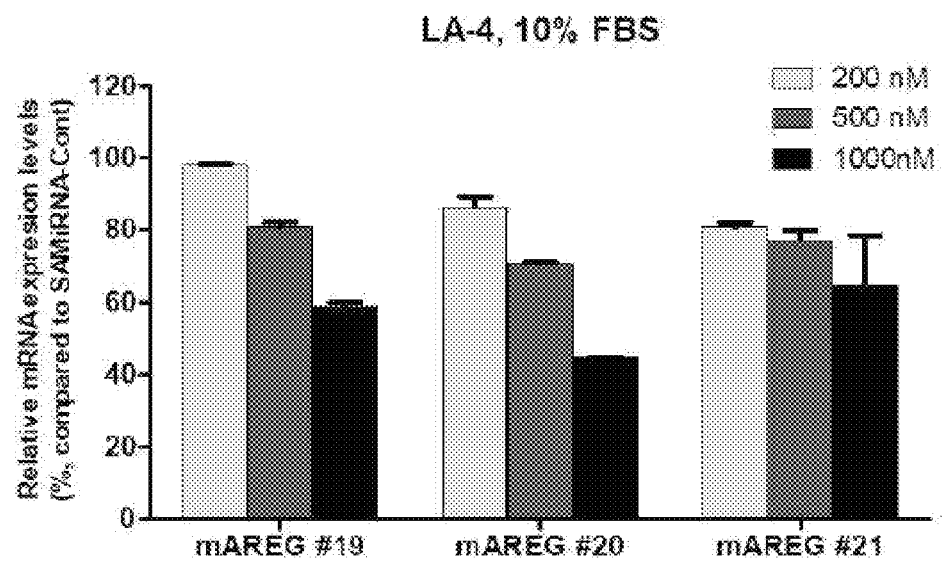
FIG. 10B shows the results of quantitatively analyzing the mRNA expression levels of mouse amphiregulin in Example 8, and is a graph showing the relative mRNA expression levels (%) of amphiregulin in the mouse lung epithelial cell line LA-4 treated with different concentrations (200, 500 and 1000 nM) of SAMiRNA having each of the sequences of SEQ ID NOs: 19, 20 and 21 of the present invention as a sense strand.

Additionally, the mouse lung epithelial cell line LA-4 was treated with each of the two selected sequences (SEQ ID NOs: 19 and 20) and the mouse SAMiRNA-amphiregulin of SEQ ID NO: 21 discovered through previous milestone studies, at treatment concentrations of 200 nM, 500 nM and 1,000 nM in cell culture media containing 10% FBS, and the expression inhibitory effects were additionally evaluated. As a result, it was confirmed again that SEQ ID NO: 20 exhibited the best expression inhibitory effect (FIG. 10B).

As shown in FIG. 10, two SAMiRNAs that most effectively inhibit amphiregulin gene expression were finally selected from 237 SAMiRNAs targeting mouse amphiregulin, and information of the sequences of the selected SAMiRNAs is shown in Table 9 below.

TABLE 8

Primer sequence information for qPCR

| Primer | Sequence |
| --- | --- |
| mGAPDH-F | AGGTCGGTGTGAACGGA TTTG (SEQ ID NO: 22) |
| mGAPDH-R | TGTAGACCATGTAGTTGAGGTCA (SEQ ID NO: 23) |
| mAREG-F | GAGGCTTCGACAAGAAAACG (SEQ ID NO: 24) |
| mAREG-R | ACCAATGTCATTTCCGGTGT (SEQ ID NO: 25) |

(F denotes a forward primer, and R denotes a reverse primer)

TABLE 9

SAMiRNA sequences that effectively inhibit mouse amphiregulin expression

| SEQ ID NO | Code Name | Position | Sense strand sequence |
| --- | --- | --- | --- |
| 19 | SAMi-mAREG#19 | 936-954 | AACGGGACTGTGCATGCCA |
| 20 | SAMi-mAREG#20 | 937-955 | ACGGGACTGTGCATGCCAT |
| 21 | SAMi-mAREG#21 | 1071-1089 | CAGTTGTCACTTTTTATGA |

Example 9. Investigation of Efficacy of SAMiRNA-mAREG by Intravenous Administration in Silica-Induced Pulmonary Fibrosis Model To analyze the efficacy of SAMi-mAREG in a pulmonary fibrosis animal model induced by silica (silicon dioxide, SIGMA, Korea), and experiment was performed. For the experiment, 7-weeks-old mice were obtained and allowed to acclimatize for 1 week. To induce the model, Silica (3 mg) was dissolved and injected intratracheally into the mice. On 3 days after the induction, mice showing no abnormal symptoms were selected and divided into a normal group, a test group to which physiological buffered saline (PBS) was administered, a test group to which SAMiRNA-Control was administered, and test groups (SAMi-mAREG #20) to which 1 mg/kg and 5 mg/kg of SAMi-mAREG #20 were respectively administered three times at intervals of 2 days. In addition, on 14 days after model induction, the mice were sacrificed.

9-1. Gene Expression Analysis for SAMiRNA in Silica-Induced Pulmonary Fibrosis Animal Model Lung tissue was obtained from the sacrificed mice and the tissue was crushed using a homogenizer. Using an RNA extraction kit (AccuPrep Cell total RNA extraction kit, BIONEER, Korea), total RNA was extracted from the cell line treated with SAMiRNA in Example 7-1 above. The extracted RNA was synthesized into cDNA in the following manner using RNA reverse transcriptase (AccuPower® RocketScript™ Cycle RT Premix with oligo (dT)20, Bioneer, Korea). Using the synthesized cDNA as a template, SYBR green real-time qPCR was performed, and the relative expression levels of total RNA in the groups were analyzed in the following manner. The synthesized cDNA was diluted 5-fold with distilled water, and for analysis of the mRNA expression level of amphiregulin, 3 μl of the diluted cDNA, 25 μl of AccuPower® 2× GreenStar™ qPCR MasterMix (BIONEER, Korea), 19 μl of distilled water, and 3 μl of amphiregulin qPCR primers (SEQ ID NOs: 24 and 25 (Table 8); 10 pmole/μl for each primer, BIONEER, Korea) were added to each well of a 96-well plate to make a mixture. Meanwhile, RPL13A, a housekeeping gene (hereinafter referred to as HK gene), was used as a standard gene to normalize the mRNA expression levels of amphiregulin, fibronectin and collagen 3α1.

After completion of the PCR, the Ct (threshold cycle) value of each target gene was corrected by the RPL13A gene, and then the ΔCt value between the groups was calculated. The relative expression levels of amphiregulin, fibronectin and collagen 3α1 genes were quantified using the ΔCt value and the equation 2(−ΔCt)×100.

As a result, it was confirmed that the expression of amphiregulin was observed decreased in the groups treated with 1 mg/kg of SAMiRNA-AREG and 5 mg/kg of SAMiRNA-AREG, respectively, compared to the silica-induced pulmonary fibrosis model group treated with physiological buffered saline and the silica-induced pulmonary fibrosis model group treated with SAMiRNA-Control. In addition, it was confirmed that fibronectin and collagen 3α1 decreased in a concentration-dependent manner in the groups treated with 1 mg/kg of SAMiRNA-AREG and 5 mg/kg of SAMiRNA-AREG, respectively, compared to the silica-induced pulmonary fibrosis model group treated with physiological buffered saline and the silica-induced pulmonary fibrosis model group treated with SAMiRNA-Control.

9-2. Histopathological Analysis for SAMiRNA in Silica-Induced Pulmonary Fibrosis Animal Model In order to verify whether SAMiRNA-AREG against the silica-induced pulmonary fibrosis model affects the expression of extracellular matrix components, immunohistochemical staining was performed. Each animal model group was sacrificed, and paraffin sections were prepared through tissue fixing, washing, dehydration, clearing, infiltration, embedding and cutting processes. The paraffin section was cut thinly with a microtome and the tissue was mounted on a slide. To observe the lung tissue pathologically, hematopoietic & eosin (H&E) staining was performed, and to examine the expression level of collagen 3α1, Masson's trichrome staining was performed. In addition, immunohistochemical staining was performed to analyze the expression level of amphiregulin.

Through hematoxylin & eosin staining, it could be seen that the silica-induced pulmonary fibrosis tissue was more damaged than the lung tissue of the normal group. However, it could be seen that the lung tissue of the mice to which SAMiRNA-AREG was administered had little damage, like the lung tissue of the normal group. In addition, Masson's trichrome staining was performed to examine the degree of fibrosis. It was confirmed that the degree of fibrosis in the lung tissue interstitium in the group to which SAMiRNA-AREG was administered decreased compared to those in the silica-induced pulmonary fibrosis model group to which physiological buffered saline (PBS) and those in the group to which SAMiRNA-Control was administered. In addition, through immunohistochemical staining for amphiregulin, it could be seen that amphiregulin was much expressed in the interstitium between the cells in the silica-induced pulmonary fibrosis animal group. However, it could be confirmed that, in the group to which SAMiRNA-AREG was administered, the expression of AREG in the lung tissue interstitium decreased.

Figure 11:
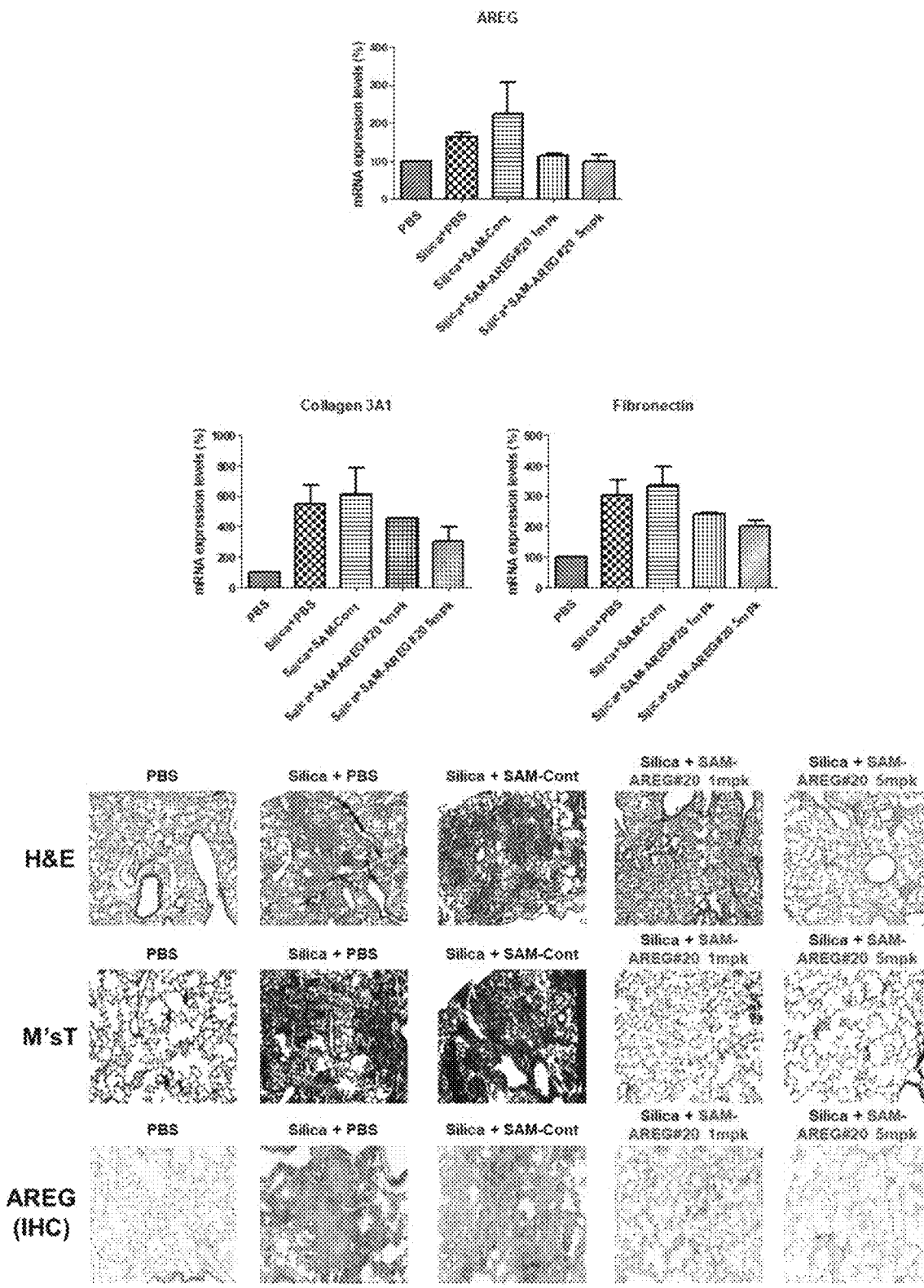
FIG. 11 depicts graphs showing the results of lung tissue staining and the relative mRNA expression levels (%) of a target gene and fibrosis marker genes after 1 mg/kg and 5 mg/kg of SAMiRNA-AREG #20 were administered intravenously to mice with silica-induced lung fibrosis in Example 9.

In conclusion, 1 mg/kg and 5 mg/kg of SAMiRNA-AREG were administered intravenously to the silica-induced pulmonary fibrosis model mice three times (days 10, 12 and 14), and evaluation of the inhibitory effect of SAMiRNA-AREG on the expression of the target gene amphiregulin and the fibrosis marker genes in the lung tissue and H&E staining and Masson's trichrome staining of the lung tissue were performed. As a result of analyzing the expression of the target gene amphiregulin and the fibrosis marker genes collagen 3α1 and fibronectin, it was confirmed that the expression was increased by silica-induced pulmonary fibrosis and it was confirmed the effect of inhibiting the expression in a concentration-dependent manner by treatment with SAMiRNA-AREG. In addition, as a result of tissue staining, it was confirmed that, in the silica-induced pulmonary fibrosis mouse treated with PBS or SAMiRNA-Control, infiltration of cells into the lung tissue and the expression of collagen increased, but in the test group treated with SAMiRNA-AREG, cellular infiltration and collagen significantly decreased to levels comparable with those in the control group treated with DPBS (FIG. 11).

In addition, immunohistochemistry staining for AREG in the silica-induced pulmonary fibrosis model was performed. As shown in FIG. 11, the expression levels of AREG in the tissues of the silica-induced pulmonary fibrosis model mice, to which 1 mg/kg and 5 mg/kg of SAMiRNA-AREG were administered, were analyzed by IHC staining. It was confirmed that, in the lung tissue of the model mice to which silica+PBS or silica+SAMi-Cont was administered, the expression of AREG in the interstitial site significantly increased compared to that in the normal lung tissue. However, as a result of analyzing the expression of AREG in the tissues to which 1 mg/kg and 5 mg/kg of SAMiRNA-AREG were administered, it could be confirmed that the expression of AREG in the tissues significantly decreased compared to that in the silica-induced pulmonary fibrosis tissue (FIG. 11).

Figure 12:
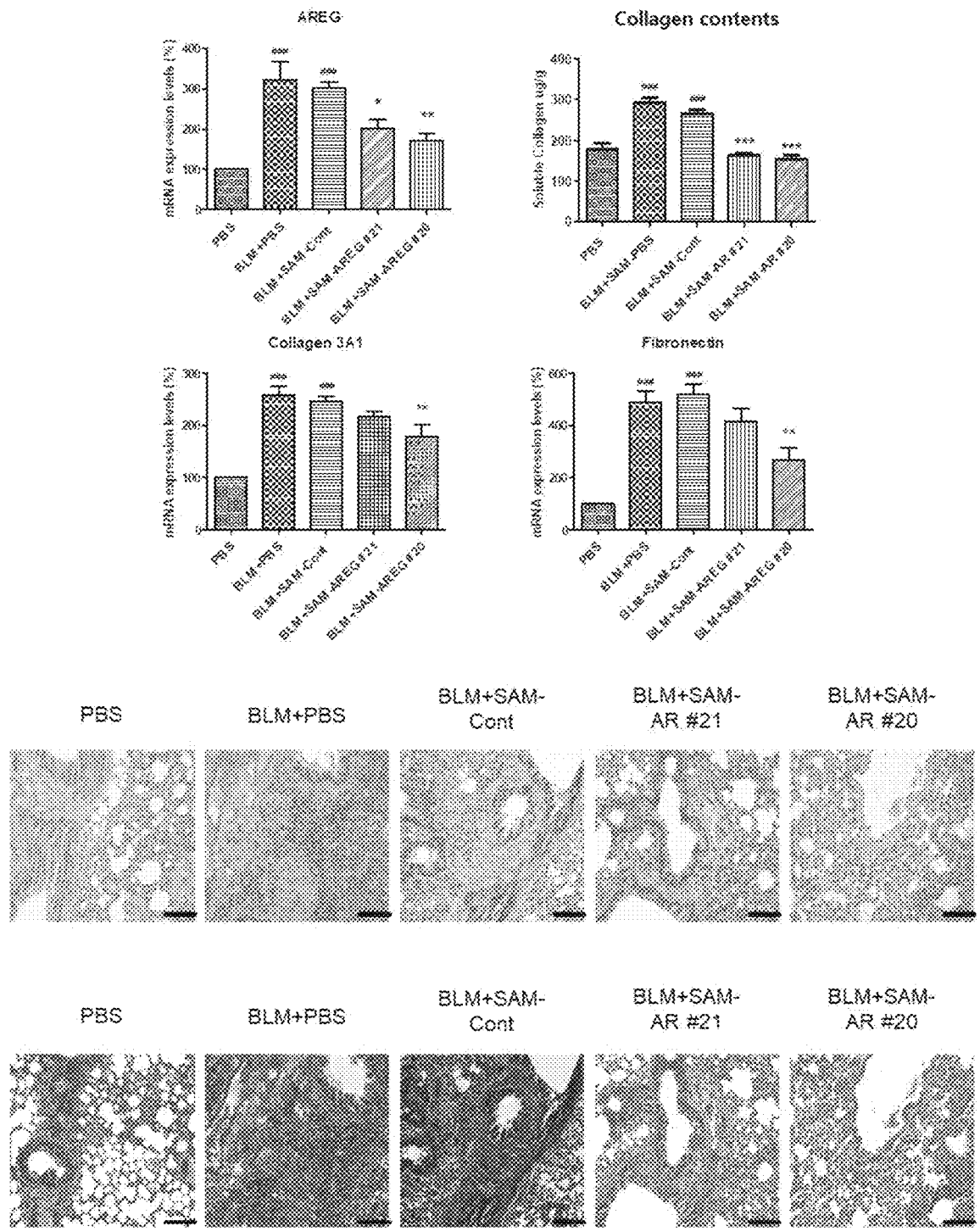
FIG. 12 depicts graphs showing the results of lung tissue staining and the relative mRNA expression levels (%) of a target gene and fibrosis marker genes after 5 mg/kg of SAMiRNA-AREG #20 was administered intravenously to mice with bleomycin-induced lung fibrosis in Example 10.
Figure 13:
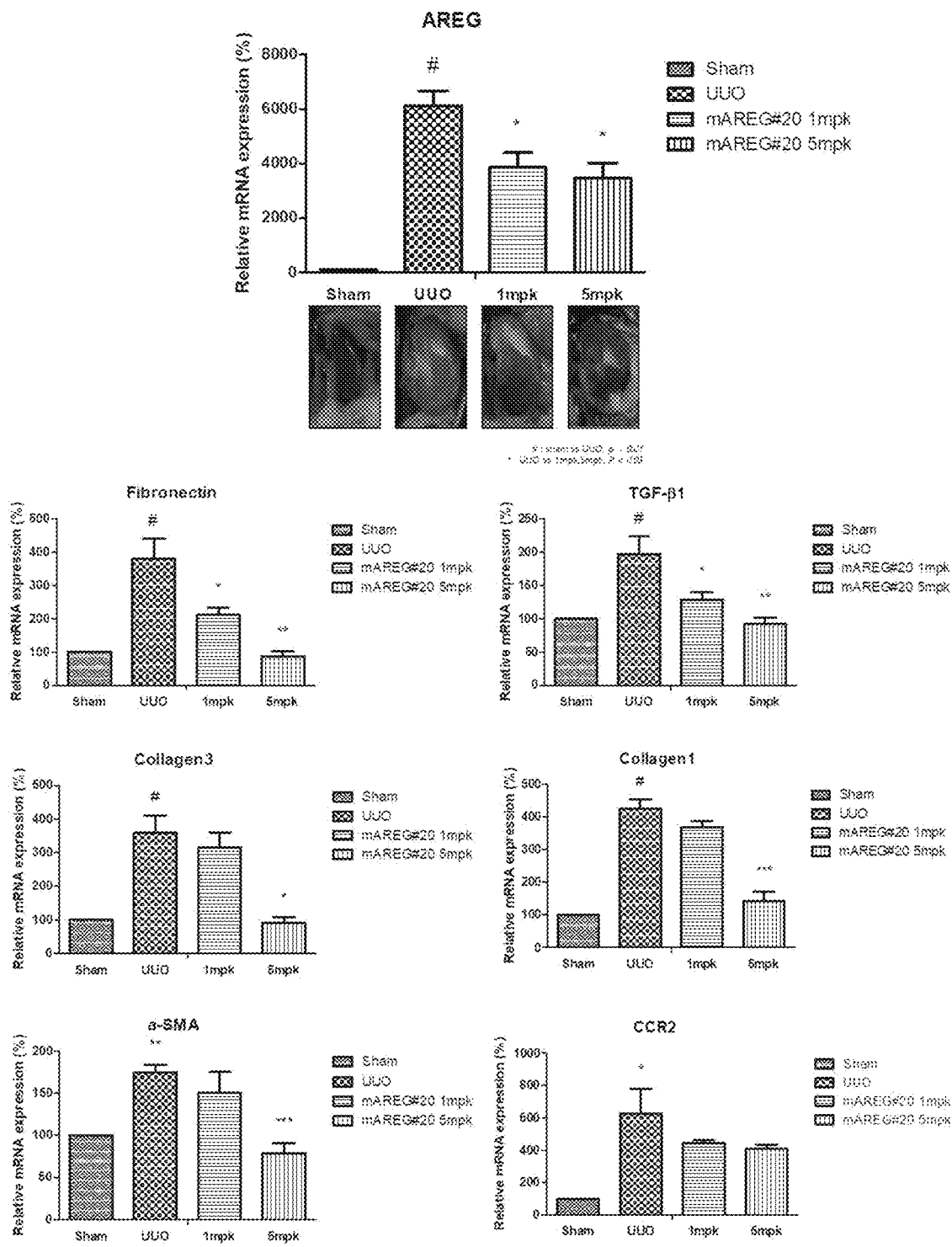
FIG. 13 depicts graphs showing the relative mRNA expression levels (%) of a target gene, fibrosis marker genes and inflammation marker genes in renal tissue after 1 mg/kg and 5 mg/kg of SAMiRNA-AREG #20 were administered intravenously to UUO model mice subjected to UUO surgery in Example 11.

Example 10. Investigation of Efficacy of SAMiRNA-mAREG by Intravenous Administration in Bleomycin-Induced Pulmonary Fibrosis Model 5 mg/kg of SAMiRNA-AREG (SAMi-mAREG #20) was administered intravenously to a bleomycin-induced pulmonary fibrosis mouse model three times (days 8, 10 and 12), and Sircol assay was performed. As a result, it was confirmed that the amount of collagen protein in the test group, to which SAMiRNA-AREG was administered, decreased by >40% compared to that in the control group SAMiRNA-Cont. In addition, RNA was extracted from the lung tissue of the same test group, and the effect of inhibiting the expression of the target gene amphiregulin and the fibrosis marker gene collagen 3α1 was analyzed. As a result, the expression inhibitory effect compared to the control was found. It was confirmed that the effect of the newly identified test substance of SEQ ID NO: 20 was equal to or higher than that of the existing sequence. H&E staining of the lung tissue and collagen 3α1-specific Masson's trichrome staining of the lung tissue were performed. As a result of tissue staining, it was confirmed that, in the bleomycin-induced pulmonary fibrosis mouse group treated with PBS or SAMiRNA-Control, infiltration of cells into the lung tissue increased and staining due to collagen accumulation increased. It was confirmed that, in the test group treated with SAMiRNA-AREG, cellular infiltration and collagen accumulation significantly decreased (FIG. 12). The tissue staining and the analysis of target gene expression were performed in the same manner as in Example 8.

Example 11. Evaluation of Effect of SAMiRNA-AREG Against Renal Fibrosis Induced by UUO (Unilateral Ureteral Obstruction) in Mice Analysis of the effect of SAMiRNA-AREG (SAMi-mAREG #20) in a renal fibrosis animal model induced by UUO surgery was performed. First, inhalation anesthesia of mice with iFran solution (Hana Pharmaceutical, Korea) was performed to prepare a renal fibrosis animal model. The skin and peritoneum were incised, and the ureter of the left kidney was tied with 4-0 silk in two positions. To prevent urinary tract infections, the middle between the two locations was cut. In addition, the right kidney was operated in the same way, but the ureter was not tied. Likewise, the abdomen of the normal group was also open, and the ureter of the left kidney was checked, but was not tied. In addition, the peritoneum and skin were sutured to prevent infection. At 6 hours after model induction, first administration of 1 mg/kg or 5 mg/kg of SAMiRNA-AREG was performed. After 24 hours, second administration was performed. Two administrations were performed, and animals were sacrificed 24 hours after the last administration. The animal model groups were a total of four groups: a normal group, an UUO model group to which physiological buffered saline was administered, and UUO groups to which 1 mg/kg and 5 mg/kg of SAMiRNA-AREG were administered, respectively.

11-1. Gene Expression Analysis for SAMiRNA in Renal Fibrosis Induced by UUO (Unilateral Ureteral Obstruction)

Lung tissue was obtained from the sacrificed mice and the tissue was crushed using a homogenizer. Using an RNA extraction kit (AccuPrep Cell total RNA extraction kit, BIONEER, Korea), total RNA was extracted from the cell line treated with SAMiRNA in Example 7-1 above. The extracted RNA was synthesized into cDNA in the following manner using RNA reverse transcriptase (AccuPower® RocketScript™ Cycle RT Premix with oligo (dT)20, Bioneer, Korea). Using the synthesized cDNA as a template, SYBR green real-time qPCR was performed, and the relative expression levels of total RNA in the groups were analyzed in the following manner. The synthesized cDNA was diluted 5-fold with distilled water, and for analysis of the mRNA expression levels of amphiregulin and fibrosis markers, 3 μl of the diluted cDNA, 25 μl of AccuPower® 2× GreenStar™ qPCR MasterMix (BIONEER, Korea), 19 μl of distilled water, and 3 μl of qPCR primers (SEQ ID NOs: 24 and 25 (Table 8); 10 pmole/μl for each primer, BIONEER, Korea) for amphiregulin and fibrosis markers were added to each well of a 96-well plate to make a mixture. Meanwhile, RPL13A, a housekeeping gene (hereinafter referred to as HK gene), was used as a standard gene to normalize the mRNA expression levels of transforming growth factor-1, amphiregulin, fibronectin, collagen 1, smooth muscle actin and collagen 3α1. In addition, the CCR2 gene was also analyze to verify efficacy against inflammatory factors.

After completion of the PCR, the Ct (threshold cycle) value of the target gene was corrected by the RPL13A gene, and then the ΔCt value between the groups was calculated. The relative expression levels of transforming growth factor-1, amphiregulin, fibronectin, collagen 1, smooth muscle actin, collagen 3α1 and CCR2 gene were quantified using the ΔCt value and the equation $2(-\Delta Ct) \times 100$.

As a result, the expression level of amphiregulin was 60 times higher in the UUO model group to which physiological buffered saline was administered than in the normal group. It was confirmed that the expression of amphiregulin gene decreased in the groups to which 1 mg/kg of SAMiRNA-AREG and 5 mg/kg of SAMiRNA-AREG were administered, respectively. In addition, it was confirmed that fibronectin and transforming growth factor-1 decreased in a concentration-dependent manner in the groups to which 1 mg/kg of SAMiRNA-AREG and 5 mg/kg of SAMiRNA-AREG were administered, respectively, compared to the UUO model group. In addition, collagen 3α1, collagen 1, and smooth muscle actin tended to decrease in the group to which 1 mg/kg of SAMiRNA-AREG was administered, compared to the UUO model group. However, it was confirmed that the effect of decreasing the expression of the genes was better in the group to which 5 mg/kg of SAMiRNA-AREG was administered than in the group to which 1 mg/kg of SAMiRNA-AREG was administered. In addition, it was confirmed that CCR2 about 6 times increased in the UUO model group, but decreased in the groups to which SAMiRNA-AREG was administered.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

The double-stranded oligonucleotide structure comprising the amphiregulin-specific double-stranded oligonucleotide according to the present invention, and a pharmaceutical composition comprising the same as an active ingredient may inhibit amphiregulin with high efficiency without side effects, and thus may exhibit excellent effects on the prevention and treatment of diseases caused by excessive fibrosis and respiratory diseases.

Sequence List Free Text

Electronic file is attached.

The invention claimed is:

1. A compound having a structure of Formula (3) or (4):

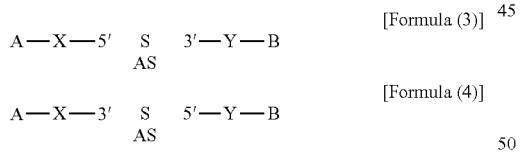

wherein A represents hexaethyleneglycol-(—PO$_3$-hexaethyleneglycol)3, B represents C$_{24}$ (C$_6$—S—S—C$_{18}$), X and Y each independently represent a simple covalent bond or a linker-mediated covalent bond, and S is a DNA sense strand and AS is an RNA antisense strand having a sequence complementary thereto, and wherein S and AS form a DNA-RNA hybrid.

2. The compound of claim 1, wherein S is an amphiregulin-specific DNA sense strand.

3. The compound of claim 2, wherein S is a DNA sense strand having a sequence selected from SEQ ID NO: 1-14 and AS is an RNA antisense strand having a sequence complementary to the DNA sense strand.

4. The compound of claim 2, wherein S is a DNA sense strand having a sequence of SEQ ID NO: 10, 11, or 12.

5. The compound of claim 4, wherein S is a DNA sense strand having a sequence of SEQ ID NO: 12.

6. The compound of claim 1, wherein the DNA sense strand or the RNA antisense strand comprises a chemical modification.

7. The compound of claim 6, wherein the chemical modification is selected from the group consisting of:
a modification in which a hydroxyl (OH) group at the 2' carbon position of a sugar structure in nucleotides is substituted with any one moiety selected from the group consisting of methyl (—CH$_3$), methoxy (—OCH$_3$), amine (—NH$_2$), fluorine (—F), —O-2-methoxyethyl, —O-propyl, —O-2-methylthioethyl, —O-3-aminopropyl, O-3-dimethylaminopropyl, —O—N-methylacetamido and —O-dimethylamidooxyethyl;
a modification in which oxygen in a sugar structure in nucleotides is substituted with sulfur;
a modification of a bond between nucleotides to any one bond selected from the group consisting of a phosphorothioate bond, a boranophosphophate bond and a methyl phosphonate bond; and
a modification to PNA (peptide nucleic acid), LNA (locked nucleic acid) or UNA (unlocked nucleic acid).

8. The compound of claim 1, wherein the covalent bond represented by X and Y is either a non-degradable bond or a degradable bond.

9. The compound of claim 8, comprising a non-degradable bond, wherein the non-degradable bond is an amide bond or a phosphate bond.

10. The compound of claim 9, comprising a degradable bond, wherein the degradable bond is selected from the group consisting of a disulfide bond, an acid-degradable bond, an ester bond, an anhydride bond, a biodegradable bond, and an enzyme-degradable bond.

11. The compound of claim 1, further comprising hexosamine, sugar or carbohydrate conjugated to A.

12. The compound of claim 1, further comprising N-acetyl galactosamine (NAG) conjugated to A.

13. The compound of claim 1, further comprising glucose or mannose conjugated to A.

14. A nanoparticle comprising the compound of claim 1.

15. The nanoparticle of claim 14, wherein the nanoparticle comprises a mixture of double-stranded oligonucleotides, wherein each double-stranded oligonucleotide has a DNA sense strand with a unique sequence.

16. A pharmaceutical composition comprising, as an active ingredient, the compound of claim 1.

17. A pharmaceutical composition comprising, as an active ingredient, the nanoparticle of claim 14.

* * * * *

UNITED STATES PATENT AND TRADEMARK OFFICE
CERTIFICATE OF CORRECTION

PATENT NO. : 12,037,589 B2
APPLICATION NO. : 18/330853
DATED : July 16, 2024
INVENTOR(S) : Kim et al.

It is certified that error appears in the above-identified patent and that said Letters Patent is hereby corrected as shown below:

In the Claims

In Column 48, in Claim 7, Line 54, delete "O-3-dimethylaminopropyl," and insert
-- —O-3-dimethylaminopropyl,-- therefor.

Signed and Sealed this
Third Day of December, 2024

Katherine Kelly Vidal
Director of the United States Patent and Trademark Office